United States Patent
Barbas, III

(10) Patent No.: US 10,030,051 B2
(45) Date of Patent: Jul. 24, 2018

(54) ANTIBODY TARGETING THROUGH A MODULAR RECOGNITION DOMAIN

(71) Applicant: The Scripps Research Institute, La Jolla, CA (US)

(72) Inventor: Carlos F. Barbas, III, La Jolla, CA (US)

(73) Assignee: The Scripps Research Institute, La Jolla, CA (US)

( * ) Notice: Subject to any disclaimer, the term of this patent is extended or adjusted under 35 U.S.C. 154(b) by 30 days.

(21) Appl. No.: 14/963,722

(22) Filed: Dec. 9, 2015

(65) Prior Publication Data

US 2016/0159863 A1    Jun. 9, 2016

Related U.S. Application Data

(60) Division of application No. 13/694,155, filed on Nov. 1, 2012, now abandoned, which is a continuation of application No. 12/747,883, filed as application No. PCT/US2008/088337 on Dec. 24, 2008, now abandoned.

(60) Provisional application No. 61/018,816, filed on Jan. 3, 2008, provisional application No. 61/022,767, filed on Jan. 22, 2008.

(51) Int. Cl.
| | |
|---|---|
| *C07K 7/06* | (2006.01) |
| *C07K 16/28* | (2006.01) |
| *C07K 19/00* | (2006.01) |
| *A61K 38/08* | (2006.01) |
| *A61K 39/395* | (2006.01) |
| *A61K 47/62* | (2017.01) |
| *A61K 47/66* | (2017.01) |
| *C07K 14/00* | (2006.01) |
| *C07K 16/32* | (2006.01) |
| *C07K 7/08* | (2006.01) |
| *C07K 16/40* | (2006.01) |
| *C12N 9/00* | (2006.01) |
| *G01N 33/68* | (2006.01) |

(52) U.S. Cl.
CPC .............. *C07K 14/00* (2013.01); *A61K 38/08* (2013.01); *A61K 39/395* (2013.01); *A61K 47/62* (2017.08); *A61K 47/66* (2017.08); *C07K 7/06* (2013.01); *C07K 7/08* (2013.01); *C07K 16/2848* (2013.01); *C07K 16/2863* (2013.01); *C07K 16/32* (2013.01); *C07K 16/40* (2013.01); *C07K 19/00* (2013.01); *C12N 9/0002* (2013.01); *G01N 33/6845* (2013.01); *C07K 2317/24* (2013.01); *C07K 2317/56* (2013.01); *C07K 2319/035* (2013.01); *C07K 2319/70* (2013.01); *C07K 2319/74* (2013.01)

(58) Field of Classification Search
None
See application file for complete search history.

(56) References Cited

U.S. PATENT DOCUMENTS

| | | |
|---|---|---|
| 5,196,193 A | 3/1993 | Carroll |
| 5,637,481 A | 6/1997 | Ledbetter et al. |
| 5,677,171 A | 10/1997 | Hudziak et al. |
| 5,720,954 A | 2/1998 | Hudziak et al. |
| 5,725,856 A | 3/1998 | Hudziak et al. |
| 5,770,195 A | 6/1998 | Hudziak et al. |
| 5,772,997 A | 6/1998 | Hudziak et al. |
| 5,821,337 A | 10/1998 | Carter et al. |
| 5,844,094 A | 12/1998 | Hudson et al. |
| 5,877,289 A | 3/1999 | Thorpe et al. |
| 5,977,322 A | 11/1999 | Marks et al. |
| 6,054,561 A | 4/2000 | Ring |
| 6,103,889 A | 8/2000 | Whitlow et al. |
| 6,132,992 A | 10/2000 | Ledbetter et al. |
| 6,165,464 A | 12/2000 | Hudziak et al. |
| 6,166,185 A | 12/2000 | Davis et al. |
| 6,194,177 B1 | 2/2001 | Campbell et al. |
| 6,267,958 B1 | 7/2001 | Andya et al. |
| 6,268,488 B1 | 7/2001 | Barbas, III et al. |
| 6,339,142 B1 | 1/2002 | Basey et al. |
| 6,387,371 B1 | 5/2002 | Hudziak et al. |
| 6,399,063 B1 | 6/2002 | Hudziak et al. |
| 6,413,932 B1 | 7/2002 | Cerretti et al. |
| 6,417,168 B1 | 7/2002 | Greene et al. |
| 6,458,356 B1 | 10/2002 | Arakawa et al. |
| 6,512,096 B2 | 1/2003 | Weiner et al. |
| 6,515,110 B1 | 2/2003 | Whitlow et al. |
| 6,521,424 B2 | 2/2003 | Cerretti et al. |
| 6,627,196 B1 | 9/2003 | Baughman et al. |

(Continued)

FOREIGN PATENT DOCUMENTS

| | | |
|---|---|---|
| EP | 1591527 A1 | 11/2005 |
| EP | 1600459 A2 | 11/2005 |

(Continued)

OTHER PUBLICATIONS

Mueller et al., Mol. Cancer Res., 2009, vol. 7(7)1078-1085.*
El-Gazzar et al., Oncogene, 2014, vol. 33(41):4932-4940.*
Asano, R., et al., "Highly Effective Recombinant Format of a Humanized IgG-like Bispecific Antibody for Cancer Immunotherapy With Retargeting of Lymphocytes to Tumor Cells," The Journal of biological chemistry 282(38):27659-27665, American Society for Biochemistry and Molecular Biology, United States (Sep. 2007).
Corte-Real, S., et al., "Intrabodies Targeting the Kaposi Sarcoma-associated Herpesvirus Latency Antigen Inhibit Viral Persistence in Lymphoma Cells," Blood 106(12):3797-3802, American Society of Hematology, United States (Dec. 2005).

(Continued)

*Primary Examiner* — Xiaozhen Xie
(74) *Attorney, Agent, or Firm* — Hugh Wang; Thomas Fitting

(57) ABSTRACT

The present invention provides antibodies containing one or more modular recognition domains (MRDs) for targeting the antibodies to specific sites. The use of the antibodies containing one or more modular recognition domains to treat disease, and methods of making antibodies containing one or more modular recognition domains are also provided in the invention.

9 Claims, 8 Drawing Sheets

(56) References Cited

U.S. PATENT DOCUMENTS

| | | |
|---|---|---|
| 6,719,971 B1 | 4/2004 | Carter et al. |
| 6,800,738 B1 | 10/2004 | Carter et al. |
| 6,821,515 B1 | 11/2004 | Cleland et al. |
| 6,884,879 B1 | 4/2005 | Baca et al. |
| 7,063,840 B2 | 6/2006 | Davis et al. |
| 7,067,475 B2 | 6/2006 | Cerretti et al. |
| 7,074,404 B2 | 7/2006 | Basey et al. |
| 7,101,580 B2 | 9/2006 | Metzger |
| 7,112,317 B2 | 9/2006 | Thorpe et al. |
| 7,125,541 B2 | 10/2006 | Thorpe et al. |
| 7,138,370 B2 | 11/2006 | Oliner et al. |
| 7,148,321 B2 | 12/2006 | Gillies et al. |
| 7,183,076 B2 | 2/2007 | Arathoon et al. |
| 7,189,830 B2 * | 3/2007 | Gillies .................. C07K 16/28 530/402 |
| 7,205,275 B2 | 4/2007 | Oliner et al. |
| 7,211,252 B2 | 5/2007 | Mundy et al. |
| 7,226,592 B2 | 6/2007 | Kreysch |
| 7,365,054 B2 | 4/2008 | Lode et al. |
| 7,371,379 B2 | 5/2008 | Baughman et al. |
| 7,449,184 B2 | 11/2008 | Allison et al. |
| 7,456,016 B2 | 11/2008 | Young et al. |
| 7,462,352 B2 | 12/2008 | Hansen et al. |
| 7,485,302 B2 | 2/2009 | Adams et al. |
| 7,521,053 B2 | 4/2009 | Oliner |
| 7,537,931 B2 | 5/2009 | Adams et al. |
| 7,541,440 B2 | 6/2009 | Goldenberg et al. |
| 7,612,181 B2 | 11/2009 | Wu et al. |
| 7,625,558 B2 | 12/2009 | Greene et al. |
| 7,638,124 B2 | 12/2009 | Reiter et al. |
| 7,645,861 B2 | 1/2010 | Gegg et al. |
| 7,655,764 B2 | 2/2010 | Gegg et al. |
| 7,655,765 B2 | 2/2010 | Gegg et al. |
| 7,662,931 B2 | 2/2010 | Gegg et al. |
| 7,666,832 B2 | 2/2010 | Oliner et al. |
| 7,666,839 B2 | 2/2010 | Oliner et al. |
| 7,682,609 B2 | 3/2010 | Andya et al. |
| 7,723,499 B2 | 5/2010 | Oliner et al. |
| 7,736,652 B2 | 6/2010 | Penichet et al. |
| 7,749,501 B2 | 7/2010 | Gelfand |
| 7,750,127 B2 | 7/2010 | Gegg et al. |
| 7,750,128 B2 | 7/2010 | Gegg et al. |
| 7,786,267 B2 | 8/2010 | Zurawski et al. |
| 7,790,674 B2 | 9/2010 | Oliner et al. |
| 7,862,817 B2 | 1/2011 | Adams et al. |
| 7,951,369 B2 | 5/2011 | Goldenberg et al. |
| 7,973,140 B2 | 7/2011 | Green et al. |
| 7,981,418 B2 | 7/2011 | Amler et al. |
| 7,993,834 B2 | 8/2011 | Mass |
| 8,008,453 B2 | 8/2011 | Gegg et al. |
| 8,454,960 B2 | 6/2013 | Barbas, III |
| 8,557,242 B2 | 10/2013 | Barbas, III |
| 8,557,243 B2 | 10/2013 | Barbas, III |
| 9,676,833 B2 | 6/2017 | Roschke et al. |
| 2003/0130496 A1 | 7/2003 | Winter et al. |
| 2003/0229023 A1 | 12/2003 | Oliner et al. |
| 2004/0001827 A1 | 1/2004 | Dennis |
| 2004/0052785 A1 | 3/2004 | Goodman et al. |
| 2004/0057969 A1 | 3/2004 | Smith et al. |
| 2005/0136044 A1 | 6/2005 | Watkins et al. |
| 2005/0287153 A1 | 12/2005 | Dennis |
| 2006/0106203 A1 | 5/2006 | Winter et al. |
| 2006/0128944 A1 | 6/2006 | Botti et al. |
| 2006/0140936 A1 | 6/2006 | Goldenberg et al. |
| 2006/0222653 A1 | 10/2006 | Abel et al. |
| 2006/0269540 A1 | 11/2006 | Robert et al. |
| 2007/0031402 A1 | 2/2007 | Zhang et al. |
| 2007/0086998 A1 | 4/2007 | Nagy |
| 2007/0166753 A1 | 7/2007 | Mass |
| 2007/0196274 A1 | 8/2007 | Sun |
| 2007/0202041 A1 | 8/2007 | Young et al. |
| 2007/0248994 A1 | 10/2007 | Su |
| 2007/0254316 A1 | 11/2007 | Rodriguez et al. |
| 2008/0233130 A1 | 9/2008 | Tomlinson et al. |
| 2008/0241145 A1 | 10/2008 | Goldenberg et al. |
| 2008/0299120 A1 | 12/2008 | Miller et al. |
| 2009/0054323 A1 | 2/2009 | Oliner et al. |
| 2009/0087432 A1 | 4/2009 | Sliwkowski |
| 2009/0148905 A1 | 6/2009 | Ashman et al. |
| 2009/0181022 A1 | 7/2009 | Nielsen et al. |
| 2009/0191212 A1 | 7/2009 | Oliner et al. |
| 2009/0226447 A1 | 9/2009 | Boone et al. |
| 2009/0226466 A1 * | 9/2009 | Fong ................ A61K 39/39558 424/178.1 |
| 2009/0246206 A1 | 10/2009 | Nielsen et al. |
| 2009/0298195 A1 | 12/2009 | Rueker et al. |
| 2009/0304694 A1 | 12/2009 | Oliner et al. |
| 2010/0016556 A1 | 1/2010 | Carter et al. |
| 2010/0021379 A1 | 1/2010 | Lam et al. |
| 2010/0021473 A1 | 1/2010 | De Angelis et al. |
| 2010/0047239 A1 | 2/2010 | Wu et al. |
| 2010/0048877 A1 | 2/2010 | Ruker et al. |
| 2010/0056439 A1 | 3/2010 | Beckmann et al. |
| 2010/0104588 A1 | 4/2010 | Dennis |
| 2010/0111967 A1 | 5/2010 | Baehner et al. |
| 2010/0158926 A1 | 6/2010 | Cartilage et al. |
| 2010/0159587 A1 | 6/2010 | Brinkmann et al. |
| 2010/0166695 A1 | 7/2010 | Bundle et al. |
| 2010/0166746 A1 | 7/2010 | Chowdhury et al. |
| 2010/0178298 A1 | 7/2010 | Lindhofer |
| 2010/0233173 A1 | 9/2010 | Wu et al. |
| 2010/0286060 A1 | 11/2010 | Oliner et al. |
| 2010/0297103 A1 | 11/2010 | Murakami |
| 2010/0322934 A1 | 12/2010 | Imhof-Jung et al. |
| 2010/0330115 A1 | 12/2010 | Zurawski et al. |
| 2011/0020332 A1 | 1/2011 | Greene et al. |
| 2011/0027286 A1 | 2/2011 | Thurston et al. |
| 2011/0044998 A1 | 2/2011 | Bedian et al. |
| 2011/0046355 A1 | 2/2011 | Himmler et al. |
| 2011/0076723 A1 | 3/2011 | Min et al. |
| 2011/0097300 A1 | 4/2011 | Van Slyke et al. |
| 2011/0097321 A1 | 4/2011 | Blakey et al. |
| 2011/0110851 A1 | 5/2011 | Chang et al. |
| 2011/0129464 A1 | 6/2011 | Adams et al. |
| 2011/0150895 A1 | 6/2011 | Ryu et al. |
| 2011/0158978 A1 | 6/2011 | Kirchner et al. |
| 2011/0189206 A1 | 8/2011 | Barbas, III |
| 2012/0020967 A1 | 1/2012 | Barbas, III |
| 2012/0034211 A1 | 2/2012 | Barbas, III |
| 2012/0058114 A1 | 3/2012 | Barbas, III |
| 2013/0303733 A1 | 11/2013 | Barbas |
| 2014/0127200 A1 | 5/2014 | Barbas, III |
| 2016/0046678 A1 | 2/2016 | Roschke et al. |
| 2017/0298106 A1 | 10/2017 | Roschke et al. |

FOREIGN PATENT DOCUMENTS

| | | |
|---|---|---|
| EP | 1517921 B1 | 6/2006 |
| EP | 1752471 B9 | 4/2009 |
| EP | 2070944 A1 | 6/2009 |
| EP | 1189641 B1 | 7/2009 |
| EP | 1210115 B1 | 8/2009 |
| EP | 1434791 B1 | 10/2009 |
| EP | 2110138 A1 | 10/2009 |
| EP | 2116262 A2 | 11/2009 |
| EP | 2272869 A2 | 1/2011 |
| EP | 2275119 A1 | 1/2011 |
| EP | 2284194 A1 | 2/2011 |
| EP | 2311849 A1 | 4/2011 |
| EP | 2316845 A1 | 5/2011 |
| EP | 2336180 A1 | 6/2011 |
| JP | 2003531588 A | 10/2003 |
| JP | 2004520344 A | 7/2004 |
| JP | 2004525630 A | 8/2004 |
| JP | 2005520853 A | 7/2005 |
| WO | WO-9524220 A1 | 9/1995 |
| WO | WO-9611269 A2 | 4/1996 |
| WO | WO-9720858 A1 | 6/1997 |
| WO | WO-9850431 A2 | 11/1998 |
| WO | WO-0181377 A2 | 11/2001 |
| WO | WO-02055106 A2 | 7/2002 |
| WO | WO-03016330 A2 | 2/2003 |
| WO | WO-03027246 A2 | 4/2003 |
| WO | WO-03057134 A2 | 7/2003 |

(56) References Cited

FOREIGN PATENT DOCUMENTS

| | | |
|---|---|---|
| WO | WO-2004032857 A2 | 4/2004 |
| WO | WO-2004032960 A1 | 4/2004 |
| WO | WO-2004032961 A1 | 4/2004 |
| WO | WO-2004092215 A2 | 10/2004 |
| WO | WO-2005023859 A1 | 3/2005 |
| WO | WO-2005070966 A2 | 8/2005 |
| WO | WO-2005117973 A2 | 12/2005 |
| WO | WO-2006020706 A2 | 2/2006 |
| WO | WO-2006036834 A2 | 4/2006 |
| WO | WO-2006063150 A2 | 6/2006 |
| WO | WO-2006072620 A1 | 7/2006 |
| WO | WO-2006078307 A1 | 7/2006 |
| WO | WO-2006091209 A2 | 8/2006 |
| WO | WO-2007001457 A2 | 1/2007 |
| WO | WO-2007016185 A2 | 2/2007 |
| WO | WO-2007019232 A2 | 2/2007 |
| WO | WO-2007024715 A2 | 3/2007 |
| WO | WO-2007060192 A1 | 5/2007 |
| WO | WO-2007066109 A1 | 6/2007 |
| WO | WO-2007068895 A1 | 6/2007 |
| WO | WO-2007075270 A2 | 7/2007 |
| WO | WO-2007136892 A2 | 11/2007 |
| WO | WO-2008003103 A2 | 1/2008 |
| WO | WO-2008019290 A2 | 2/2008 |
| WO | WO-2008088658 A2 | 7/2008 |
| WO | WO-2008116293 A1 | 10/2008 |
| WO | WO-2008132568 A2 | 11/2008 |
| WO | WO-2008144029 A1 | 11/2008 |
| WO | WO-2009088805 A2 | 7/2009 |
| WO | WO-2009097325 A1 | 8/2009 |
| WO | WO-2009105269 A1 | 8/2009 |
| WO | WO-2009132876 A1 | 11/2009 |
| WO | WO-2009158432 A2 | 12/2009 |
| WO | WO-2010010551 A2 | 1/2010 |
| WO | WO-2010040508 A1 | 4/2010 |
| WO | WO-2010066836 A2 | 6/2010 |
| WO | WO-2010108153 A2 | 9/2010 |
| WO | WO-2011014469 A1 | 2/2011 |
| WO | WO-2012009705 A1 | 1/2012 |

OTHER PUBLICATIONS

Dennis, M.S., et al., "Albumin Binding as a General Strategy for Improving the Pharmacokinetics of Proteins," The Journal of Biological Chemistry 277(38):35035-35043, American Society for Biochemistry and Molecular Biology, United States (Sep. 2002).
Grzesik, W.J., et al., "Synthetic Integrin-binding Peptides Promote Adhesion and Proliferation of Human Periodontal Ligament Cells in Vitro," International & American Associations for Dental Research 77(8):1606-1612, Sage, United States (Aug. 1998).
International Preliminary Report on Patentability for Application Serial No. PCT/US08/88337, dated Jul. 6, 2010, 18 pages.
International Search Report for International Application No. PCT/US08/88337, ISA/US Alexandria, Virginia, dated Jul. 20, 2009, 6 pages.
Kutty, G., et al., "Identification of a New Member of Transforming Growth Factor-beta Superfamily in Drosophila: the First Invertebrate Activin Gene," Biochemical and biophysical research communications 246(3):644-649, Elsevier, United States (May 1998).
Li, L.S., et al., "Chemical Adaptor Immunotherapy: Design, Synthesis, and Evaluation of Novel Integrin-targeting Devices," Journal of medicinal chemistry 47(23):5630-5640, American Chemical Society, United States (Nov. 2004).
Niu, G., et al., "Human Epidermal Growth Factor Receptor 2 Regulates Angiopoietin-2 Expression in Breast Cancer via Akt and Mitogen-activated Protein Kinase Pathways," Cancer Research 67(4):1487-1493, American Association for Cancer Research, United States (Feb. 2007).
Riemer, A.B., et al., "Matching of Trastuzumab (Herceptin) Epitope Mimics Onto the Surface of Her-2/neu—a New Method of Epitope Definition," Molecular Immunology 42(9):1121-1124, Pergamon Press, England (2005).
Ruoslahti, E., "Integrins," The Journal of Clinical Investigation 87(1):1-5, American Society for Clinical Investigation, United States (Jan. 1991).
Stancovski, I., et al., "Mechanistic aspects of the opposing effects of monoclonal antibodies to the ERBB2 receptor on tumor growth," Proceedings of the National Academy of Sciences USA 88(19):8691-8695, National Academy of Sciences, United States (1991).
Taipale, J. and Keski-Oja, J., et al., "Growth Factors in the Extracellular Matrix," FASEB journal : official publication of the Federation of American Societies for Experimental Biology 11(1):51-59, The Federation, United States (Jan. 1997).
Yu, L., et al., "Interaction Between Bevacizumab and Murine VEGF-A: A Reassessment," Investigative ophthalmology & visual science 49(2):522-527, Association for Research in Vision and Ophthalmology, United States (Feb. 2008).
Abraham, S., et al., "Synthesis of the Next-generation Therapeutic Antibodies that Combine Cell Targeting and Antibody-catalyzed Prodrug Activation," Proceedings of the National Academy of Sciences of the United States of America 104(13):5584-5589, National Academy of Sciences, United States (Mar. 2007).
Colman, P.M., "Effects of Amino Acid Sequence Changes on Antibody-antigen Interactions," Research in Immunology 145(1):33-36, Elsevier, France (Jan. 1994).
Conner, J.P., et al., "Ex Vivo Evaluation of Anti-EpCAM Immunocytokine HuKs-IL2 in Ovarian Cancer," Journal of immunotherapy 27(3):211-219, Lippincott-Raven, c1997-, United States (May-Jun. 2004).
Dela Cruz, J.S., et al., "Recombinant Anti-human HER2/neu IgG3-(GM-CSF) Fusion Protein Retains Antigen Specificity and Cytokine Function and Demonstrates Antitumor Activity," Journal of immunology 165(9):5112-5121, American Association of Immunologists, United States (Nov. 2000).
Doppalapudi, V.R., et al., "Chemically Programmed Antibodies: Endothelin Receptor Targeting CovX-bodies," Bioorganic & medicinal chemistry letters 17(2):501-506, Elsevier Science Ltd, England (Jan. 2007).
Dufner, P., et al, "Harnessing Phage and Ribosome Display for Antibody Optimisation," Trends in Biotechnology 24(11):523-529, Elsevier Science, England (2006).
El-Gazzar, A., et al., "Effects on Tumor Development and Metastatic Dissemination by the NKG2D Lymphocyte Receptor Expressed on Cancer Cells," Oncogene 33(41):4932-4940, Nature Publishing Group, England (Oct. 2014).
Helguera, G., et al., "Vaccination With Novel Combinations of Anti-HER2/neu Cytokines Fusion Proteins and Soluble Protein Antigen Elicits a Protective Immune Response Against HER2/neu Expressing Tumors," Vaccine 24(3):304-316, Elsevier Science, Netherlands (Jan. 2006).
Huang, H.,et al., "Angiopoietin-2 Antagonistic CovX-BodyTM Inhibits Tumor Growth and Reduces Microvessel Density," American Association for Cancer Research 48:509 (Apr. 2007).
Imanishi, Y., et al., "Angiopoietin-2 Stimulates Breast Cancer Metastasis Through the Alpha(5)beta(1) Integrin-mediated Pathway," Cancer Research 67(9):4254-4263, American Association for Cancer Research, United States (May 2007).
Landon, L.A. and Deutscher, S.L., et al., "Combinatorial Discovery of Tumor Targeting Peptides Using Phage Display," Journal of cellular biochemistry 90(3):509-517, Wiley-Liss, United States (Oct. 2003).
Luettich, K., et al., "TGFbeta1 Activates C-Jun and Erk1 via Alphavbeta6 Integrin," Molecular Cancer 2:33, BioMed Central, England (Sep. 2003).
Mueller, J., et al., "Targeting of Tumor Blood Vessels: A Phage-displayed Tumor-homing Peptide Specifically Binds to Matrix Metalloproteinase-2-processed Collagen Iv and Blocks Angiogenesis in Vivo," American Association for Cancer Research, United States 7(7):1078-1085, American Association for Cancer Research, United States (Jul. 2009).
Schraa, A.J., et al., "RGD-modified Anti-CD3 Antibodies Redirect Cytolytic Capacity of Cytotoxic T Lymphocytes Toward Alphavbeta3-expressing Endothelial Cells," International journal of cancer 112(2):279-285, Wiley-Liss, United States (Nov. 2004).

(56) References Cited

OTHER PUBLICATIONS

Serini, G., et al., "Integrins and Angiogenesis: A Sticky Business," Experimental cell research 312(5):651-658, Academic Press, United States (Mar. 2006).
Co-pending U.S. Appl. No. 15/589,585, inventors Roschke. V., et al., filed May 8, 2017 (Not Published).
Office Action dated Jun. 19, 2012, in U.S. Appl. No. 13,135,754 (now U.S. Pat. No. 8,454,960), Barbas, C.F., et al., filed Jul. 14, 2011, 8 pages.
Office Action dated Nov. 14, 2012, in U.S. Appl. No. 13/135,786 (now U.S. Pat. No. 8,557,242), Barbas, C.F., et al., filed Jul. 14, 2011, 28 pages.
Office Action dated Nov. 13, 2012, in U.S. Appl. No. 13/135,788 (now U.S. Pat. No. 8,574,577), Barbas, C.F., et al., filed Jul. 14, 2011, 28 pages.
Office Action dated Nov. 14, 2012, in U.S. Appl. No. 13/135,789 (now U.S. Pat. No. 8,557,243), Barbas, C.F., et al., filed Jul. 14, 2011, 33 pages.
Office Action dated May 4, 2015, in U.S. Appl. No. 13/815,632, Barbas, C.F., filed Mar. 13, 2013, 32 pages.
Office Action dated Nov. 4, 2015, in U.S. Appl. No. 13/815,632, Barbas, C.F., filed Mar. 13, 2013, 43 pages.
Office Action dated Sep. 14, 2016, in U.S. Appl. No. 13/815,632, Barbas, C.F., filed Mar. 13, 2013, 48 pages.
Office Action dated Aug. 9, 2017, in U.S. Appl. No. No. 13/815,632, Barbas, C.F., filed Mar. 13, 2013, 24 pages.
Office Action dated Sep. 18, 2015, in U.S. Appl. No. 14/053,860, Barbas, C.F., filed Oct. 15, 2013, 24 pages.
Office Action dated May 18, 2016, in U.S. Appl. No. 14/053,860, Barbas, C.F., filed Oct. 15, 2013, 34 pages.
Office Action dated Apr. 12, 2017, in U.S. Appl. No. 14/053,860, Barbas, C.F., filed Oct. 15, 2013, 37 pages.
Office Action for Chinese Patent Application No. 200880127584.1, dated Aug. 18, 2017, The State Intellectual Property Office of China, Beijing, China, 5 pages and English translation of the same, dated Aug. 18, 2017, 7 pages.

* cited by examiner

```
                        SEQUENCE LISTING

<160> NUMBER OF SEQ ID NOS: 58

<210> SEQ ID NO 1
    <211> LENGTH: 4
    <212> TYPE: PRT
    <213> ORGANISM: Artificial Sequence
    <220> FEATURE:
    <223> OTHER INFORMATION: Synthetic construct

<400> SEQUENCE: 1

Gly Gly Gly Ser
    1

<210> SEQ ID NO 2
    <211> LENGTH: 15
    <212> TYPE: PRT
    <213> ORGANISM: Artificial Sequence
    <220> FEATURE:
    <223> OTHER INFORMATION: Synthetic construct

<400> SEQUENCE: 2

Ser Ser Gly Gly Gly Gly Ser Gly Gly Gly Gly Gly Gly Ser Ser
    1               5                   10                  15

<210> SEQ ID NO 3
    <211> LENGTH: 7
    <212> TYPE: PRT
    <213> ORGANISM: Artificial Sequence
    <220> FEATURE:
    <223> OTHER INFORMATION: Synthetic construct

<400> SEQUENCE: 3

Tyr Cys Arg Gly Asp Cys Thr
    1               5

<210> SEQ ID NO 4
    <211> LENGTH: 7
    <212> TYPE: PRT
    <213> ORGANISM: Artificial Sequence
    <220> FEATURE:
    <223> OTHER INFORMATION: Synthetic construct

<400> SEQUENCE: 4

Pro Cys Arg Gly Asp Cys Leu
    1               5

<210> SEQ ID NO 5
    <211> LENGTH: 7
    <212> TYPE: PRT
    <213> ORGANISM: Artificial Sequence
    <220> FEATURE:
    <223> OTHER INFORMATION: Synthetic construct
```

```
<400> SEQUENCE: 5

Thr Cys Arg Gly Asp Cys Tyr
1               5

<210> SEQ ID NO 6
<211> LENGTH: 7
<212> TYPE: PRT
<213> ORGANISM: Artificial Sequence
<220> FEATURE:
<223> OTHER INFORMATION: Synthetic construct

<400> SEQUENCE: 6

Leu Cys Arg Gly Asp Cys Phe
1               5

<210> SEQ ID NO 7
<211> LENGTH: 28
<212> TYPE: PRT
<213> ORGANISM: Artificial Sequence
<220> FEATURE:
<223> OTHER INFORMATION: Synthetic construct

<400> SEQUENCE: 7

Met Gly Ala Gln Thr Asn Phe Met Pro Met Asp Asp Leu Glu Gln Arg
1               5                   10                  15

Leu Tyr Glu Gln Phe Ile Leu Gln Gln Gly Leu Glu
            20                  25

<210> SEQ ID NO 8
<211> LENGTH: 28
<212> TYPE: PRT
<213> ORGANISM: Artificial Sequence
<220> FEATURE:
<223> OTHER INFORMATION: Synthetic construct

<400> SEQUENCE: 8

Met Gly Ala Gln Thr Asn Phe Met Pro Met Asp Asn Asp Glu Leu Leu
1               5                   10                  15

Leu Tyr Glu Gln Phe Ile Leu Gln Gln Gly Leu Glu
            20                  25

<210> SEQ ID NO 9
<211> LENGTH: 28
<212> TYPE: PRT
<213> ORGANISM: Artificial Sequence
<220> FEATURE:
<223> OTHER INFORMATION: Synthetic construct

<400> SEQUENCE: 9

Met Gly Ala Gln Thr Asn Phe Met Pro Met Asp Ala Thr Glu Thr Arg
1               5                   10                  15

Leu Tyr Glu Gln Phe Ile Leu Gln Gln Gly Leu Glu
            20                  25

<210> SEQ ID NO 10
<211> LENGTH: 54
<212> TYPE: PRT
<213> ORGANISM: Artificial Sequence
<220> FEATURE:
<223> OTHER INFORMATION: Synthetic construct

<400> SEQUENCE: 10

Ala Gln Gln Glu Glu Cys Glu Trp Asp Pro Trp Thr Cys Glu His Met
1               5                   10                  15
```

Gly Ser Gly Ser Ala Thr Gly Gly Ser Gly Ser Thr Ala Ser Ser Gly
            20                  25                  30

Ser Gly Ser Ala Thr His Gln Glu Glu Cys Glu Trp Asp Pro Trp Thr
                35                  40                  45

Cys Glu His Met Leu Glu
            50

<210> SEQ ID NO 11
<211> LENGTH: 28
<212> TYPE: PRT
<213> ORGANISM: Artificial Sequence
<220> FEATURE:
<223> OTHER INFORMATION: Synthetic construct

<400> SEQUENCE: 11

Met Gly Ala Gln Thr Asn Phe Met Pro Met Asp Asn Asp Glu Leu Leu
1               5                   10                  15

Asn Tyr Glu Gln Phe Ile Leu Gln Gln Gly Leu Glu
            20                  25

<210> SEQ ID NO 12
<211> LENGTH: 10
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid

<400> SEQUENCE: 12

Pro Xaa Asp Asn Asp Xaa Leu Leu Asn Tyr
1               5                   10

<210> SEQ ID NO 13
<211> LENGTH: 19
<212> TYPE: PRT
<213> ORGANISM: Artificial Sequence
<220> FEATURE:
<223> OTHER INFORMATION: Synthetic construct

<400> SEQUENCE: 13

Val Glu Pro Asn Cys Asp Ile His Val Met Trp Glu Trp Glu Cys Phe
1               5                   10                  15

Glu Arg Leu

<210> SEQ ID NO 14
<211> LENGTH: 27
<212> TYPE: PRT
<213> ORGANISM: Artificial Sequence
<220> FEATURE:
<223> OTHER INFORMATION: Synthetic construct

<400> SEQUENCE: 14

Ser Phe Tyr Ser Cys Leu Glu Ser Leu Val Asn Gly Pro Ala Glu Lys
1               5                   10                  15

Ser Arg Gly Gln Trp Asp Gly Cys Arg Lys Lys
            20                  25

```
<210> SEQ ID NO 15
<211> LENGTH: 11
<212> TYPE: PRT
<213> ORGANISM: Artificial Sequence
<220> FEATURE:
<223> OTHER INFORMATION: Synthetic construct

<400> SEQUENCE: 15

Ala Cys Asp Cys Arg Gly Asp Cys Phe Cys Gly
1               5                   10

<210> SEQ ID NO 16
<211> LENGTH: 58
<212> TYPE: PRT
<213> ORGANISM: Artificial Sequence
<220> FEATURE:
<223> OTHER INFORMATION: Synthetic construct

<400> SEQUENCE: 16

Val Asp Asn Lys Phe Asn Lys Glu Leu Glu Lys Ala Tyr Asn Glu Ile
1               5                   10                  15

Arg Asn Leu Pro Asn Leu Asn Gly Trp Gln Met Thr Ala Phe Ile Ala
            20                  25                  30

Ser Leu Val Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 17
<211> LENGTH: 58
<212> TYPE: PRT
<213> ORGANISM: Artificial Sequence
<220> FEATURE:
<223> OTHER INFORMATION: Synthetic construct

<400> SEQUENCE: 17

Val Asp Asn Lys Phe Asn Lys Glu Met Trp Ile Ala Trp Glu Glu Ile
1               5                   10                  15

Arg Asn Leu Pro Asn Leu Asn Gly Trp Gln Met Thr Ala Phe Ile Ala
            20                  25                  30

Ser Leu Val Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 18
<211> LENGTH: 58
<212> TYPE: PRT
<213> ORGANISM: Artificial Sequence
<220> FEATURE:
<223> OTHER INFORMATION: Synthetic construct

<400> SEQUENCE: 18

Val Asp Asn Lys Phe Asn Lys Glu Met Arg Asn Ala Tyr Trp Glu Ile
1               5                   10                  15

Ala Leu Leu Pro Asn Leu Asn Asn Gln Gln Lys Arg Ala Phe Ile Arg
            20                  25                  30

Ser Leu Tyr Asp Asp Pro Ser Gln Ser Ala Asn Leu Leu Ala Glu Ala
        35                  40                  45

Lys Lys Leu Asn Asp Ala Gln Ala Pro Lys
    50                  55
```

```
<210> SEQ ID NO 19
<211> LENGTH: 18
<212> TYPE: PRT
<213> ORGANISM: Artificial Sequence
<220> FEATURE:
<223> OTHER INFORMATION: Synthetic construct

<400> SEQUENCE: 19

Ser Ser Gly Gly Gly Ser Gly Gly Gly Gly Gly Ser Ser Arg
1               5                   10                  15

Ser Ser

<210> SEQ ID NO 20
<211> LENGTH: 60
<212> TYPE: PRT
<213> ORGANISM: Artificial Sequence
<220> FEATURE:
<223> OTHER INFORMATION: Synthetic construct

<400> SEQUENCE: 20

Met Gly Ala Gln Thr Asn Phe Met Pro Met Asp Asn Asp Glu Leu Leu
1               5                   10                  15

Leu Tyr Glu Gln Phe Ile Leu Gln Gln Gly Leu Glu Gly Gly Ser Gly
                20                  25                  30

Ser Thr Ala Ser Ser Gly Ser Gly Ser Ser Leu Gly Ala Gln Thr Asn
            35                  40                  45

Phe Met Pro Met Asp Asn Asp Glu Leu Leu Leu Tyr
        50                  55                  60

<210> SEQ ID NO 21
<211> LENGTH: 16
<212> TYPE: PRT
<213> ORGANISM: Artificial Sequence
<220> FEATURE:
<223> OTHER INFORMATION: Synthetic construct

<400> SEQUENCE: 21

Ala Gln Gln Glu Glu Cys Glu Phe Ala Pro Trp Thr Cys Glu His Met
1               5                   10                  15

<210> SEQ ID NO 22
<211> LENGTH: 106
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(50)
<223> OTHER INFORMATION: Xaa can be any naturally occurring amino acid
<220> FEATURE:
<221> NAME/KEY: misc_feature
<222> LOCATION: (57)..(106)
<223> OTHER INFORMATION: Xaa can be any naturally occurring amino acid

<400> SEQUENCE: 22

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
                20                  25                  30

Xaa Xaa Xaa Xaa Xaa Xaa Xaa Xaa Xaa Xaa Xaa Xaa Xaa Xaa Xaa Xaa
            35                  40                  45

Xaa Xaa Glu Phe Ala Pro Trp Thr Xaa Xaa Xaa Xaa Xaa Xaa Xaa Xaa
        50                  55                  60
```

```
Xaa Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa
            85                  90                  95

Xaa Xaa Xaa Xaa Xaa Xaa Xaa Xaa Xaa Xaa
            100                 105

<210> SEQ ID NO 23
<211> LENGTH: 54
<212> TYPE: PRT
<213> ORGANISM: Artificial Sequence
<220> FEATURE:
<223> OTHER INFORMATION: Synthetic construct

<400> SEQUENCE: 23

Ala Gln Gln Glu Glu Cys Glu Phe Ala Pro Trp Thr Cys Glu His Met
1               5                   10                  15

Gly Ser Gly Ser Ala Thr Gly Gly Ser Gly Ser Thr Ala Ser Ser Gly
            20                  25                  30

Ser Gly Ser Ala Thr His Gln Glu Glu Cys Glu Phe Ala Pro Trp Thr
        35                  40                  45

Cys Glu His Met Leu Glu
    50

<210> SEQ ID NO 24
<211> LENGTH: 16
<212> TYPE: PRT
<213> ORGANISM: Artificial Sequence
<220> FEATURE:
<223> OTHER INFORMATION: Synthetic construct

<400> SEQUENCE: 24

Ala Gln Gln Glu Glu Cys Glu Leu Ala Pro Trp Thr Cys Glu His Met
1               5                   10                  15

<210> SEQ ID NO 25
<211> LENGTH: 106
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(50)
<223> OTHER INFORMATION: Xaa can be any naturally occurring amino acid
<220> FEATURE:
<221> NAME/KEY: misc_feature
<222> LOCATION: (57)..(106)
<223> OTHER INFORMATION: Xaa can be any naturally occurring amino acid

<400> SEQUENCE: 25

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa
        35                  40                  45

Xaa Xaa Glu Leu Ala Pro Trp Thr Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa
            85                  90                  95
```

Xaa Xaa Xaa Xaa Xaa Xaa Xaa Xaa Xaa Xaa
            100                 105

<210> SEQ ID NO 26
<211> LENGTH: 54
<212> TYPE: PRT
<213> ORGANISM: Artificial Sequence
<220> FEATURE:
<223> OTHER INFORMATION: Synthetic construct

<400> SEQUENCE: 26

Ala Gln Gln Glu Glu Cys Glu Leu Ala Pro Trp Thr Cys Glu His Met
1               5                   10                  15

Gly Ser Gly Ser Ala Thr Gly Gly Ser Gly Ser Thr Ala Ser Ser Gly
            20                  25                  30

Ser Gly Ser Ala Thr His Gln Glu Glu Cys Glu Leu Ala Pro Trp Thr
        35                  40                  45

Cys Glu His Met Leu Glu
    50

<210> SEQ ID NO 27
<211> LENGTH: 16
<212> TYPE: PRT
<213> ORGANISM: Artificial Sequence
<220> FEATURE:
<223> OTHER INFORMATION: Synthetic construct

<400> SEQUENCE: 27

Ala Gln Gln Glu Glu Cys Glu Phe Ser Pro Trp Thr Cys Glu His Met
1               5                   10                  15

<210> SEQ ID NO 28
<211> LENGTH: 106
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(50)
<223> OTHER INFORMATION: Xaa can be any naturally occurring amino acid
<220> FEATURE:
<221> NAME/KEY: misc_feature
<222> LOCATION: (57)..(106)
<223> OTHER INFORMATION: Xaa can be any naturally occurring amino acid

<400> SEQUENCE: 28

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

Xaa Xaa Glu Phe Ser Pro Trp Thr Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa Xaa
                85                  90                  95

Xaa Xaa Xaa Xaa Xaa Xaa Xaa Xaa Xaa Xaa
            100                 105

```
<210> SEQ ID NO 29
<211> LENGTH: 54
<212> TYPE: PRT
<213> ORGANISM: Artificial Sequence
<220> FEATURE:
<223> OTHER INFORMATION: Synthetic construct

<400> SEQUENCE: 29

Ala Gln Gln Glu Glu Cys Glu Phe Ser Pro Trp Thr Cys Glu His Met
1               5                   10                  15

Gly Ser Gly Ser Ala Thr Gly Gly Ser Gly Ser Thr Ala Ser Ser Gly
            20                  25                  30

Ser Gly Ser Ala Thr His Gln Glu Glu Cys Glu Phe Ser Pro Trp Thr
        35                  40                  45

Cys Glu His Met Leu Glu
    50

<210> SEQ ID NO 30
<211> LENGTH: 16
<212> TYPE: PRT
<213> ORGANISM: Artificial Sequence
<220> FEATURE:
<223> OTHER INFORMATION: Synthetic construct

<400> SEQUENCE: 30

Ala Gln Gln Glu Glu Cys Glu Leu Glu Pro Trp Thr Cys Glu His Met
1               5                   10                  15

<210> SEQ ID NO 31
<211> LENGTH: 106
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(50)
<223> OTHER INFORMATION: Xaa can be any naturally occurring amino acid
<220> FEATURE:
<221> NAME/KEY: misc_feature
<222> LOCATION: (57)..(106)
<223> OTHER INFORMATION: Xaa can be any naturally occurring amino acid

<400> SEQUENCE: 31

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

Xaa Xaa Glu Leu Glu Pro Trp Thr Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa
                85                  90                  95

Xaa Xaa Xaa Xaa Xaa Xaa Xaa Xaa Xaa Xaa
            100                 105

<210> SEQ ID NO 32
<211> LENGTH: 54
<212> TYPE: PRT
<213> ORGANISM: Artificial Sequence
<220> FEATURE:
```

<223> OTHER INFORMATION: Synthetic construct

<400> SEQUENCE: 32

Ala Gln Gln Glu Glu Cys Glu Leu Glu Pro Trp Thr Cys Glu His Met
1               5                   10                  15

Gly Ser Gly Ser Ala Thr Gly Gly Ser Gly Ser Thr Ala Ser Ser Gly
            20                  25                  30

Ser Gly Ser Ala Thr His Gln Glu Glu Cys Glu Leu Glu Pro Trp Thr
        35                  40                  45

Cys Glu His Met Leu Glu
    50

<210> SEQ ID NO 33
<211> LENGTH: 54
<212> TYPE: PRT
<213> ORGANISM: Artificial Sequence
<220> FEATURE:
<223> OTHER INFORMATION: Synthetic construct

<400> SEQUENCE: 33

Ala Gln Gln Glu Glu Cys Glu Phe Ala Pro Trp Thr Cys Glu His Met
1               5                   10                  15

Gly Ser Gly Ser Ala Thr Gly Gly Ser Gly Ser Thr Ala Ser Ser Gly
            20                  25                  30

Ser Gly Ser Ala Thr His Gln Glu Glu Cys Glu Leu Ala Pro Trp Thr
        35                  40                  45

Cys Glu His Met Leu Glu
    50

<210> SEQ ID NO 34
<211> LENGTH: 54
<212> TYPE: PRT
<213> ORGANISM: Artificial Sequence
<220> FEATURE:
<223> OTHER INFORMATION: Synthetic construct

<400> SEQUENCE: 34

Ala Gln Gln Glu Glu Cys Glu Phe Ala Pro Trp Thr Cys Glu His Met
1               5                   10                  15

Gly Ser Gly Ser Ala Thr Gly Gly Ser Gly Ser Thr Ala Ser Ser Gly
            20                  25                  30

Ser Gly Ser Ala Thr His Gln Glu Glu Cys Glu Phe Ser Pro Trp Thr
        35                  40                  45

Cys Glu His Met Leu Glu
    50

<210> SEQ ID NO 35
<211> LENGTH: 28
<212> TYPE: PRT
<213> ORGANISM: Artificial Sequence
<220> FEATURE:
<223> OTHER INFORMATION: Synthetic construct

<400> SEQUENCE: 35

Asn Phe Tyr Gln Cys Ile Glu Met Leu Ala Ser His Pro Ala Glu Lys
1               5                   10                  15

Ser Arg Gly Gln Trp Gln Glu Cys Arg Thr Gly Gly
            20                  25

<210> SEQ ID NO 36
<211> LENGTH: 28

```
<212> TYPE: PRT
<213> ORGANISM: Artificial Sequence
<220> FEATURE:
<223> OTHER INFORMATION: Synthetic construct

<400> SEQUENCE: 36

Asn Phe Tyr Gln Cys Ile Glu Gln Leu Ala Leu Arg Pro Ala Glu Lys
1               5                   10                  15

Ser Arg Gly Gln Trp Gln Glu Cys Arg Thr Gly Gly
            20                  25

<210> SEQ ID NO 37
<211> LENGTH: 28
<212> TYPE: PRT
<213> ORGANISM: Artificial Sequence
<220> FEATURE:
<223> OTHER INFORMATION: Synthetic construct

<400> SEQUENCE: 37

Asn Phe Tyr Gln Cys Ile Asp Leu Leu Met Ala Tyr Pro Ala Glu Lys
1               5                   10                  15

Ser Arg Gly Gln Trp Gln Glu Cys Arg Thr Gly Gly
            20                  25

<210> SEQ ID NO 38
<211> LENGTH: 28
<212> TYPE: PRT
<213> ORGANISM: Artificial Sequence
<220> FEATURE:
<223> OTHER INFORMATION: Synthetic construct

<400> SEQUENCE: 38

Asn Phe Tyr Gln Cys Ile Glu Arg Leu Val Thr Gly Pro Ala Glu Lys
1               5                   10                  15

Ser Arg Gly Gln Trp Gln Glu Cys Arg Thr Gly Gly
            20                  25

<210> SEQ ID NO 39
<211> LENGTH: 28
<212> TYPE: PRT
<213> ORGANISM: Artificial Sequence
<220> FEATURE:
<223> OTHER INFORMATION: Synthetic construct

<400> SEQUENCE: 39

Asn Phe Tyr Gln Cys Ile Glu Tyr Leu Ala Met Lys Pro Ala Glu Lys
1               5                   10                  15

Ser Arg Gly Gln Trp Gln Glu Cys Arg Thr Gly Gly
            20                  25

<210> SEQ ID NO 40
<211> LENGTH: 28
<212> TYPE: PRT
<213> ORGANISM: Artificial Sequence
<220> FEATURE:
<223> OTHER INFORMATION: Synthetic construct

<400> SEQUENCE: 40

Asn Phe Tyr Gln Cys Ile Glu Ala Leu Gln Ser Arg Pro Ala Glu Lys
1               5                   10                  15

Ser Arg Gly Gln Trp Gln Glu Cys Arg Thr Gly Gly
            20                  25

<210> SEQ ID NO 41
```

-continued

```
<211> LENGTH: 28
<212> TYPE: PRT
<213> ORGANISM: Artificial Sequence
<220> FEATURE:
<223> OTHER INFORMATION: Synthetic construct

<400> SEQUENCE: 41

Asn Phe Tyr Gln Cys Ile Glu Ala Leu Ser Arg Ser Pro Ala Glu Lys
1               5                   10                  15

Ser Arg Gly Gln Trp Gln Glu Cys Arg Thr Gly Gly
            20                  25

<210> SEQ ID NO 42
<211> LENGTH: 27
<212> TYPE: PRT
<213> ORGANISM: Artificial Sequence
<220> FEATURE:
<223> OTHER INFORMATION: Synthetic construct

<400> SEQUENCE: 42

Asn Phe Tyr Gln Cys Ile Glu His Leu Ser Gly Ser Pro Ala Glu Lys
1               5                   10                  15

Ser Arg Gly Gln Trp Gln Glu Cys Arg Thr Gly
            20                  25

<210> SEQ ID NO 43
<211> LENGTH: 27
<212> TYPE: PRT
<213> ORGANISM: Artificial Sequence
<220> FEATURE:
<223> OTHER INFORMATION: Synthetic construct

<400> SEQUENCE: 43

Asn Phe Tyr Gln Cys Ile Glu Ser Leu Ala Gly Gly Pro Ala Glu Lys
1               5                   10                  15

Ser Arg Gly Gln Trp Gln Glu Cys Arg Thr Gly
            20                  25

<210> SEQ ID NO 44
<211> LENGTH: 27
<212> TYPE: PRT
<213> ORGANISM: Artificial Sequence
<220> FEATURE:
<223> OTHER INFORMATION: Synthetic construct

<400> SEQUENCE: 44

Asn Phe Tyr Gln Cys Ile Glu Ala Leu Val Gly Val Pro Ala Glu Lys
1               5                   10                  15

Ser Arg Gly Gln Trp Gln Glu Cys Arg Thr Gly
            20                  25

<210> SEQ ID NO 45
<211> LENGTH: 27
<212> TYPE: PRT
<213> ORGANISM: Artificial Sequence
<220> FEATURE:
<223> OTHER INFORMATION: Synthetic construct

<400> SEQUENCE: 45

Asn Phe Tyr Gln Cys Ile Glu Met Leu Ser Leu Pro Pro Ala Glu Lys
1               5                   10                  15

Ser Arg Gly Gln Trp Gln Glu Cys Arg Thr Gly
            20                  25
```

```
<210> SEQ ID NO 46
<211> LENGTH: 27
<212> TYPE: PRT
<213> ORGANISM: Artificial Sequence
<220> FEATURE:
<223> OTHER INFORMATION: Synthetic construct

<400> SEQUENCE: 46

Asn Phe Tyr Gln Cys Ile Glu Val Phe Trp Gly Arg Pro Ala Glu Lys
1               5                   10                  15

Ser Arg Gly Gln Trp Gln Glu Cys Arg Thr Gly
            20                  25

<210> SEQ ID NO 47
<211> LENGTH: 27
<212> TYPE: PRT
<213> ORGANISM: Artificial Sequence
<220> FEATURE:
<223> OTHER INFORMATION: Synthetic construct

<400> SEQUENCE: 47

Asn Phe Tyr Gln Cys Ile Glu Gln Leu Ser Ser Gly Pro Ala Glu Lys
1               5                   10                  15

Ser Arg Gly Gln Trp Gln Glu Cys Arg Thr Gly
            20                  25

<210> SEQ ID NO 48
<211> LENGTH: 27
<212> TYPE: PRT
<213> ORGANISM: Artificial Sequence
<220> FEATURE:
<223> OTHER INFORMATION: Synthetic construct

<400> SEQUENCE: 48

Asn Phe Tyr Gln Cys Ile Glu Leu Leu Ser Ala Arg Pro Ala Glu Lys
1               5                   10                  15

Ser Arg Gly Gln Trp Ala Glu Cys Arg Ala Gly
            20                  25

<210> SEQ ID NO 49
<211> LENGTH: 27
<212> TYPE: PRT
<213> ORGANISM: Artificial Sequence
<220> FEATURE:
<223> OTHER INFORMATION: Synthetic construct

<400> SEQUENCE: 49

Asn Phe Tyr Gln Cys Ile Glu Ala Leu Ala Arg Thr Pro Ala Glu Lys
1               5                   10                  15

Ser Arg Gly Gln Trp Val Glu Cys Arg Ala Pro
            20                  25

<210> SEQ ID NO 50
<211> LENGTH: 18
<212> TYPE: DNA
<213> ORGANISM: Artificial Sequence
<220> FEATURE:
<223> OTHER INFORMATION: Synthetic construct

<400> SEQUENCE: 50
gtggagtgca gggcgccg                                                 18

<210> SEQ ID NO 51
<211> LENGTH: 6
<212> TYPE: PRT
```

```
<213> ORGANISM: Artificial Sequence
<220> FEATURE:
<223> OTHER INFORMATION: Synthetic construct

<400> SEQUENCE: 51

Val Glu Cys Arg Ala Pro
1               5

<210> SEQ ID NO 52
<211> LENGTH: 18
<212> TYPE: DNA
<213> ORGANISM: Artificial Sequence
<220> FEATURE:
<223> OTHER INFORMATION: Synthetic construct

<400> SEQUENCE: 52
gctgagtgca gggctggg                                                 18

<210> SEQ ID NO 53
<211> LENGTH: 6
<212> TYPE: PRT
<213> ORGANISM: Artificial Sequence
<220> FEATURE:
<223> OTHER INFORMATION: Synthetic construct

<400> SEQUENCE: 53

Ala Glu Cys Arg Ala Gly
1               5

<210> SEQ ID NO 54
<211> LENGTH: 18
<212> TYPE: DNA
<213> ORGANISM: Artificial Sequence
<220> FEATURE:
<223> OTHER INFORMATION: Synthetic construct

<400> SEQUENCE: 54
caggagtgca ggacgggg                                                 18

<210> SEQ ID NO 55
<211> LENGTH: 6
<212> TYPE: PRT
<213> ORGANISM: Artificial Sequence
<220> FEATURE:
<223> OTHER INFORMATION: Synthetic construct

<400> SEQUENCE: 55

Gln Glu Cys Arg Thr Gly
1               5

<210> SEQ ID NO 56
<211> LENGTH: 26
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (12)..(26)
<223> OTHER INFORMATION: Xaa can be any naturally occurring amino acid

<400> SEQUENCE: 56

Met Gly Ala Gln Thr Asn Phe Met Pro Met Asp Xaa Xaa Xaa Xaa Xaa
1               5                   10                  15

Xaa Xaa Xaa Xaa Xaa Xaa Xaa Xaa Xaa Xaa
            20                  25
```

<210> SEQ ID NO 57
<211> LENGTH: 116
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(50)
<223> OTHER INFORMATION: Xaa can be any naturally occurring amino acid
<220> FEATURE:
<221> NAME/KEY: misc_feature
<222> LOCATION: (58)..(59)
<223> OTHER INFORMATION: Xaa can be any naturally occurring amino acid
<220> FEATURE:
<221> NAME/KEY: misc_feature
<222> LOCATION: (67)..(116)
<223> OTHER INFORMATION: Xaa can be any naturally occurring amino acid

<400> SEQUENCE: 57

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa
        35                  40                  45

Xaa Xaa Ala Gln Gln Glu Glu Cys Glu Xaa Xaa Pro Trp Thr Cys Glu
    50                  55                  60

His Met Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa
            85                  90                  95

Xaa Xaa Xaa Xaa Xaa Xaa Xaa Xaa Xaa Xaa Xaa Xaa Xaa Xaa Xaa
        100                 105                 110

Xaa Xaa Xaa Xaa
        115

<210> SEQ ID NO 58
<211> LENGTH: 28
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (7)..(7)
<223> OTHER INFORMATION: Xaa is E or D
<220> FEATURE:
<221> NAME/KEY: misc_feature
<222> LOCATION: (8)..(8)
<223> OTHER INFORMATION: Xaa can be any naturally occurring amino acid
<220> FEATURE:
<221> NAME/KEY: misc_feature
<222> LOCATION: (10)..(12)
<223> OTHER INFORMATION: Xaa can be any naturally occurring amino acid

<400> SEQUENCE: 58

Asn Phe Tyr Gln Cys Ile Xaa Xaa Leu Xaa Xaa Xaa Pro Ala Glu Lys
1               5                   10                  15

Ser Arg Gly Gln Trp Gln Glu Cys Arg Thr Gly Gly
            20                  25

ANTIBODY TARGETING THROUGH A MODULAR RECOGNITION DOMAIN

CROSS-REFERENCE TO RELATED APPLICATIONS

This application is a Divisional of U.S. application Ser. No. 13/694,155 (filed Nov. 1, 2012; now abandoned), which is a Continuation of U.S. application Ser. No. 12/747,883 (filed Nov. 23, 2010; now abandoned), which is a national stage application of PCT International Application No. PCT/US2008/088337 (filed Dec. 24, 2008; now abandoned), which claims the benefit of priority to U.S. Provisional Application 61/018,816 (filed Jan. 3, 2008; now abandoned) and U.S. Provisional Application 61/022,767 (filed Jan. 22, 2008; now abandoned). The disclosure of each of the aforementioned applications is incorporated herein by reference in its entirety and for all purposes.

FIELD OF THE INVENTION

This invention relates generally to antibodies containing one or more modular recognition domains and more specifically to the use of the antibodies containing one or more modular recognition domains to treat disease, and methods of making antibodies containing one or more modular recognition domains.

BACKGROUND

Catalytically active monoclonal antibodies (Abs) can be used for selective prodrug activation and chemical transformations. Monoclonal Abs with aldolase activity have emerged as highly efficient catalysts for a number of chemical transformations, particularly aldol and retro-aldol reactions. The retro-aldolase activity of Abs, such as 38C2 and 93F3, have allowed researchers to design, synthesize, and evaluate prodrugs of various chemotherapeutic agents that can be activated by retro-aldol reactions. (Construction of 38C2 was described in WO 97/21803, herein incorporated by reference). 38C2 contains an antibody combining site that catalyzes the aldol addition reaction between an aliphatic donor and an aldehyde acceptor. In a syngeneic mouse model of neuroblastoma, systemic administration of an etoposide prodrug and intra-tumor injection of 38C2 inhibited tumor growth.

One drawback in the use of catalytic Abs is that they lack a device to target the catalytic Ab to the malignant cells. Previous studies demonstrated that in an antibody-directed enzyme prodrug therapy (ADEPT) or antibody-directed abzyme prodrug therapy (ADAPT) approach, enzymes or catalytic antibodies can be directed to tumor cells by chemical conjugation or recombinant fusion to targeting antibodies. However, a more efficient alternative would be using the catalytic antibody fused to a targeting peptide located outside the antibody combining site, thereby leaving the active site available for the prodrug activation. For example, the fusion of Ab 38C2 to an integrin αvβ3-binding peptide would selectively localize the antibody to the tumor and/or the tumor vasculature and trigger prodrug activation at that site. The potential therapy of this approach is supported by preclinical and phase III clinical data suggesting that peptides can be converted into viable drugs through fusion to antibody Fc regions.

The development of bispecific or multi-specific antibodies that target two or more cancer targets simultaneously and or activate prodrugs offers a novel and promising solution to attacking cancer and other diseases. Such antibodies are exemplified in FIG. 1 of the present application. Studies of bispecific antibodies (BsAb) that simultaneously target two tumor-associated antigens (e.g. growth factor receptors) for down-regulation of multiple cell proliferation/survival pathways has provided support for this approach. Traditionally, bispecific antibodies have been prepared by chemically linking two different monoclonal antibodies or by fusing two hybridoma cell lines to produce a hybrid-hybridoma. Dual-specific, tetravalent IgG-like molecules, or dual-variable-domain immunoglobins, have been engineered from two monoclonal antibodies. These dual-variable-domain immunoglobins are capable of binding both antigens in the presence of serum. However, these approaches present challenges with respect to manufacturing, yield and purity.

A variety of recombinant methods have been developed for efficient production of small BsAb fragments such as diabody, minibody, and Fab-scFv fusion proteins. These BsAb fragments may possess some advantages over the full-length IgG-like molecules for certain clinical applications, such as for tumor radio-imaging and targeting, because of better tissue penetration and faster clearance from the circulation. On the other hand, IgG-like BsAb may prove to be preferred over smaller BsAb fragments for other in vivo applications, specifically for oncology indications, by providing the Fc domain that confers long serum half-life and supports secondary immune function, such as antibody-dependent cellular cytotoxicity and complement-mediated cytotoxicity. Unlike their fragment counterparts, engineering and production of recombinant IgG-like BsAb has been, however, rather technically challenging due to their large size (~150-200 kDa) and structural complexity. Success in the field, as judged by successful application in animal models, has been very limited. Recently, with the examination of a variety of constructs, the efficient expression of Fc domain containing BsAb molecules in mammalian cells has made some strides.

Another approach that has been used to target antibodies is through the use of peptibodies. Peptibodies are essentially peptide fusions with antibody Fc regions. Given the success of studies using random peptide libraries to find high-affinity peptide ligands for a wide variety of targets, fusion of such peptides to antibody Fc regions provides a means of making peptides into therapeutic candidates by increasing their circulatory half-life and activity through increased valency.

Protein interactions with other molecules is basic to biochemistry. Protein interactions include receptor-ligand interactions, antibody-antigen interactions, cell-cell contact and pathogen interactions with target tissues. Protein interactions can involve contact with other proteins, with carbohydrates, oligosaccharides, lipids, metal ions and the like materials. The basic unit of protein interaction is the region of the protein involved in contact and recognition, and is referred to as the binding site or target site.

Peptides derived from phage display libraries typically retain their binding characteristics when linked to other molecules. Specific peptides of this type can be treated as modular specificity blocks or molecular recognition domains (MRDs) that can be combined to create a single protein with binding specificities for several defined targets.

An example of a such a defined target site is integrin. Integrins are a family of transmembrane cell adhesion receptors that are composed of α and β subunits and mediate cell attachment to proteins within the extracellular matrix. At present, eighteen α and eight β subunits are known; these form 24 different αβ heterodimers with different specificities for various ECM cell-adhesive proteins. Ligands for various integrins include fibronectin, collagen, laminin, von Willebrand factor, osteopontin, thrombospondin, and vitronectin, which are all components of the ECM. Certain integrins can also bind to soluble ligands such as fibrinogen or to other adhesion molecules on adjacent cells. Integrins are known to exist in distinct activation states that exhibit different affinities for ligand. Recognition of soluble ligands by integrins strictly depends on specific changes in receptor conformation. This provides a molecular switch that controls the ability of cells to aggregate in an integrin dependent manner and to arrest under the dynamic flow conditions of the vasculature. This mechanism is well established for leukocytes and platelets that circulate within the blood stream in a resting state while expressing non-activated integrins. Upon stimulation through proinflammatory or prothrombotic agonists, these cell types promptly respond with a number of molecular changes including the switch of key integrins, β2 integrins for leucocytes and αvβ3 for platelets, from "resting" to "activated" conformations. This enables these cell types to arrest within the vasculature, promoting cell cohesion and leading to thrombus formation.

It has been demonstrated that a metastatic subset of human breast cancer cells expresses integrin αvβ3 in a constitutively activated form. This aberrant expression of αvβ3 plays a role in metastasis of breast cancer as well as prostate cancer, melanoma, and neuroblastic tumors. The activated receptor strongly promotes cancer cell migration and enables the cells to arrest under blood flow conditions. In this way, activation of αvβ3 endows metastatic cells with key properties likely to be critical for successful dissemination and colonization of target organs. Tumor cells that have successfully entered a target organ may further utilize αvβ3 to thrive in the new environment, as αvβ3 matrix interactions can promote cell survival and proliferation. For example, αvβ3 binding to osteopontin promotes malignancy and elevated levels of osteopontin correlate with a poor prognosis in breast cancer.

For these reasons, and for its established role in angiogenesis, the αvβ3 integrin is one of the most widely studied integrins. Antagonists of this molecule have significant potential for use in targeted drug delivery. One approach that has been used to target αvβ3 integrin uses the high binding specificity to αvβ3 of peptides containing the Arg-Gly-Asp (RGD) sequence. This tripeptide, naturally present in extracellular matrix proteins, is the primary binding site of the αvβ3 integrin. However, RGD based reporter probes are problematic due to fast blood clearance, high kidney and liver uptake and fast tumor washout. Chemical modification of cyclised RGD peptides has been shown to increase their stability and valency. These modified peptides are then coupled to radio-isotypes and used either for tumor imaging or to inhibit tumor growth.

Integrin αvβ3 is one of the most well characterized integrin heterodimers and is one of several heterodimers that have been implicated in tumor-induced angiogenesis. While sparingly expressed in mature blood vessels, αvβ3 is significantly up-regulated during angiogenesis in vivo. The expression of αvβ3 correlates with aggressiveness of disease in breast and cervical cancer as well as in malignant melanoma. Recent studies suggest that αvβ3 may be useful as a diagnostic or prognostic indicator for some tumors. Integrin αvβ3 is particularly attractive as a therapeutic target due to its relatively limited cellular distribution. It is not generally expressed on epithelial cells, and minimally expressed on other cell types. Furthermore, αvβ3 antagonists, including both cyclic RGD peptides and monoclonal antibodies, significantly inhibit cytokine-induced angiogenesis and the growth of solid tumor on the chick chorioallantoic membrane.

Another integrin heterodimer, αvβ5, is more widely expressed on malignant tumor cells and is likely involved in VEGF-mediated angiogenesis. It has been shown that αvβ3 and αvβ5 promote angiogenesis via distinct pathways: αvβ3 through bFGF and TNF-a, and αvβ5 through VEGF and TGF-α. It has also been shown that inhibition of Src kinase can block VEGF-induced, but not FGF2-induced, angiogenesis. These results strongly imply that FGF2 and VEGF activate different angiogenic pathways that require αvβ3 and αvβ5, respectively.

Integrins have also been implicated in tumor metastasis. Metastasis is the primary cause of morbidity and mortality in cancer. Malignant progression of melanoma, glioma, ovarian, and breast cancer have all been strongly linked with the expression of the integrin αvβ3 and in some cases with αvβ5. More recently, it has been shown that activation of integrin αvβ3 plays a significant role in metastasis in human breast cancer. A very strong correlation between expression of αvβ3 and breast cancer metastasis has been noted where normal breast epithelia are αvβ3 negative and approximately 50% of invasive lobular carcinomas and nearly all bone metastases in breast cancer express αvβ3. Antagonism of αvβ3 with a cyclic peptide has been shown to synergize with radioimmunotherapy in studies involving breast cancer xenografts.

Angiogenesis, the formation of new blood vessels from existing ones, is essential to may physiological and pathological processes. Normally, angiogenesis is tightly regulated by pro- and anti-angiogenic factors, but in the case of diseases such as cancer, ocular neovascular disease, arthritis and psoriasis, the process can go awry. The association of angiogenesis with disease has made the discovery of anti-angiogenic compound attractive. The most promising phage derived anti-angiogenic peptide described to date, developed by Amgen, neutralizes the angiogenic cytokine Ang2.

While the VEGFs and their receptors have been among the most extensively targeted molecules in the angiogenesis field, preclinical efforts targeting the more recently discovered angiopoietin-Tie2 pathway are underway. Both protein families involve ligand receptor interactions, and both include members whose functions are largely restricted postnatally to endothelial cells and some hematopoietic stem cell lineages. Tie-2 is a receptor tyrosine kinase with four known ligands, angiopoietin-1 (Ang1) through angiopoietin-4 (Ang4), the best studied being Ang1 and Ang2. Ang1 stimulates phosphorylation of Tie2 and the Ang2 interaction with Tie2 has been shown to both antagonize and agonize Tie2 receptor phosphorylation. Elevated Ang2 expression at sites of normal and pathological postnatal angiogenesis circumstantially implies a proangiogenic role for Ang2. Vessel-selective Ang2 induction associated with angiogenesis has been demonstrated in diseases including cancer. In patients with colon carcinoma, Ang2 is expressed ubiquitously in tumor epithelium, whereas expression of Ang1 in tumor epithelium was shown to be rare. The net gain of Ang2 activity has been suggested to be an initiating factor for tumor angiogenesis.

Other fusion proteins directed towards cellular receptors are under clinical evaluation. Herceptin (Trastuzumab), developed by Genentech, is a recombinant humanized monoclonal antibody directed against the extracellular domain of the human epidermal tyrosine kinase receptor 2 (HER2 or ErbB2). The HER2 gene is overexpressed in 25% of invasive breast cancers, and is associated with poor prognosis and altered sensitivity to chemotherapeutic agents. Herceptin blocks the proliferation of ErbB2-overexpressing breast cancers, and is currently the only ErbB2 targeted antibody therapy approved by the FDA for the treatment of ErbB2 over-expressing metastatic breast cancer (MBC). In normal adult cells, few ErbB2 molecules exist at the cell surface ~20,000 per cell, so few heterodimers are formed and growth signals are relatively weak and controllable. When ErbB2 is overexpressed, ~500,000 per cell, multiple ErbB2 heterodimers are formed and cell signaling is stronger, resulting in enhanced responsiveness to growth factors and malignant growth. This explains why ErbB2 overexpression is an indicator of poor prognosis in breast tumors and may be predictive of response to treatment.

ErbB2 is a promising and validated target for breast cancer, where it is found both in primary tumor and metastatic sites. Herceptin induces rapid removal of ErbB2 from the cell surface, thereby reducing its availability to heterodimerize and promote growth. Mechanisms of action of Herceptin observed in experimental in vitro and in vivo models include inhibition of proteolysis of ErbB2's extracellular domain, disruption of downstream signaling pathways such as phosphatidylinositiol 3-kinase (PI3K) and mitogen-activated protein kinase (MAPK) cascades, GI cell-cycle arrest, inhibition of DNA repair, suppression of angiogenesis and induction of antibody dependent cellular cytotoxicity (ADCC). The majority of patients with metastatic breast cancer who initially respond to Herceptin, however, demonstrate disease progression within one year of treatment initiation.

Another target cellular receptor is type 1 insulin-like growth factor-1 receptor (IGF-1R), IGF-1R is a receptor-tyrosine kinase that plays a critical role in signaling cell survival and proliferation. The IGF system is frequently deregulated in cancer cells by the establishment of autocrine loops involving IGF-I or -II and/or IGF-1R overexpression. Moreover, epidemiological studies have suggested a link between elevated IGF levels and the development of major human cancers, such as breast, colon, lung and prostate cancer. Expression of IGFs and their cognate receptors has been correlated with disease stage, reduced survival, development of metastases and tumor de-differentiation.

Besides IGF-1R, epidermal growth factor receptor (EGFR) has also been implicated in the tumorigenesis of numerous cancers. Effective tumor inhibition has been achieved both experimentally and clinically with a number of strategies that antagonize either receptor activity. Because of the redundancy of growth signaling pathways in tumor cells, inhibition of one receptor function (e.g. EGFR) could be effectively compensated by up-regulation of other growth factor receptor (e.g. IGF-1R)-mediated pathways. For example, a recent study has shown that malignant glioma cell lines expressing equivalent EGFR had significantly different sensitivity to EGFR inhibition depending on their capability of activating IGF-1R and its downstream signaling pathways. Other studies have also demonstrated that overexpression and/or activation of IGF-1R in tumor cells might contribute to their resistance to chemotherapeutic agents, radiation, or antibody therapy such as Herceptin. And consequently, inhibition of IGF-1R signaling has resulted in increased sensitivity of tumor cells to Herceptin.

EGFR is a receptor tyrosine kinase that is expressed on many normal tissues as well as neoplastic lesions of most organs. Overexpression of EGFR or expression of mutant forms of EGFR has been observed in many tumors, particularly epithelial tumors, and is associated with poor clinical prognosis. Inhibition of signaling through this receptor induces an anti-tumor effect. With the FDA approval of Cetuximab, also known as Erbitux (a mouse/human chimeric antibody) in February of 2004, EGFR became an approved antibody drug target for the treatment of metastatic colorectal cancer. In March of 2006, Erbitux also received FDA approval for the treatment squamous cell carcinoma of the head and neck (SCCHN). More recently, Vectibix, a fully human antibody directed against EGFR, was approved for metastatic colorectal cancer. Neither drug is a stand-alone agent in colorectal cancer—they were approved as add-ons to existing colorectal regimens. In colorectal cancer, Erbitux is given in combination with the drug irinotecan and Vectibix is administered after disease progression on, or following fluoropyrimidine-, oxaliplatin-, and irinotecan-containing chemotherapy regimens. Erbitux has been approved as a single agent in recurrent or metastatic SCCHN only where prior platinum-based chemotherapy has failed. Advanced clinical trials which use these drugs to target non-small cell lung carcinoma are ongoing. The sequence of Erbitux or the EGFR antibody, is well known in the art (see for example, Goldstein, et al., Clin. Cancer Res. 1:1311, 1995; U.S. Pat. No. 6,217,866), herein incorporated by reference.

An obstacle in the utilization of a catalytic antibody for selective prodrug activation in cancer therapy has been systemic tumor targeting. The present invention describes an approach based on the adaptation of target binding peptides, or modular recognition domains (MRDs), which are fused to full length antibodies that effectively target tumor cells or soluble molecules while retaining the prodrug activation capability of the catalytic antibody. Since the MRDs are fused to the antibody so as not to significantly mitigate binding to the antibody's traditional binding site, the antibody's specificity remains intact after MRD addition.

As noted in FIG. 2, MRDs, designated by triangles, circles, and squares, can be appended on any of the termini of either heavy or light chains of a typical antibody. The first schematic represents a simple peptibody with a peptide fused to the C-terminus of an Fc. This approach provided for the preparation of bi-, tri-, tetra, and penta-specific antibodies. Display of a single MRD at each N- and C-termini of an IgG provides for octavalent display of the MRD. As an alternative to the construction of bi- and multifunctional antibodies through the combination of antibody variable domains, high-affinity peptides selected from phage display libraries or derived from natural ligands may offer a highly versatile and modular approach to the construction of multifunctional antibodies that retain both the binding and half-life advantages of traditional antibodies. MRDs can also extend the binding capacity of non-catalytic antibodies, providing for an effective approach to extend the binding functionality of antibodies, particularly for therapeutic purposes.

SUMMARY

The present invention is directed towards a full length antibody comprising a modular recognition domain (MRD). Also embodied in the present invention are variants and deriviatives of such antibodies comprising a MRD.

In one aspect, the antibody and the MRD are operably linked through a linker peptide. In one aspect, the linker peptide is between 2 to 20 peptides long, or between 4 to 10 or about 4 to 15 peptides long. In one aspect of the present invention, the linker peptide comprises the sequence GGGS (SEQ ID. NO.:1), the sequence SSGGGGSGGGGGGSS (SEQ ID. NO.: 2), or the sequence SSG GGGSGGGGGGSSRSS (SEQ ID NO.: 19). Other linkers containing a core sequence GGGS as shown in SEQ ID NO:1 are included herein wherein the linker peptide is from about 4-20 amino acids.

According to another embodiment of the present invention, the MRD is operably linked to the C-terminal end of the heavy chain of the antibody. In another aspect, the MRD is operably linked to the N-terminal end of the heavy chain of the antibody. In yet another aspect, the MRD is operably linked to the C-terminal end of the light chain of the antibody. In another aspect, the MRD is operably linked to the N-terminal end of the light chain of the antibody. In another aspect, two or more MRDs are operably linked to any terminal end of the antibody. In another aspect, two or more MRDs are operably linked to two or more terminal ends of the antibody.

In one embodiment of the present invention, the target of the MRD is a cellular antigen. In one embodiment of the present invention, the target of the MRD is CD20.

In one embodiment of the present invention, the target of the MRD is an integrin. In one aspect, the peptide sequence of the integrin targeting MRD is YCRGDCT (SEQ ID. NO.:3). In another aspect, the peptide sequence of the integrin targeting MRD is PCRGDCL (SEQ ID. NO.:4). In yet another aspect, the peptide sequence of the integrin targeting MRD is TCRGDCY (SEQ ID. NO.:5). In another aspect, the peptide sequence of the integrin targeting MRD is LCRGDCF (SEQ ID. NO.:6).

In one embodiment of the present invention, the target of the MRD is an angiogenic cytokine. In one aspect, the peptide sequence of the angiogenic cytokine targeting MRD is MGAQTNFMPMDDLEQRLYEQFILQQGLE (SEQ ID. NO.:7). In another aspect, the peptide sequence of the angiogenic cytokine targeting MRD is MGAQTNFMPMDNDELLLYEQFILQQGLE (SEQ ID. NO.:8). In yet another aspect, the peptide sequence of the angiogenic cytokine targeting MRD is MGAQTNFMPMDATETRLYEQFILQQGLE (SEQ ID. NO.:9). In another aspect, the peptide sequence of the angiogenic cytokine targeting MRD is AQQEECEWDPWTCEHMGSGSATGGSGSTASSGSGSATHQEECEWDPWTCEHMLE (SEQ ID. NO.:10). In another aspect, the peptide sequence of the angiogenic cytokine targeting MRD is MGAQTNFMPMDNDELLNYEQFILQQGLE (SEQ ID. NO.: 11). In another aspect, the peptide sequence of the angiogenic cytokine targeting MRD is PXDNDXLLNY (SEQ ID. NO.: 12), where X is one of the 20 naturally-occurring amino acids. In another embodiment, the targeting MRD peptide has the core sequence MGAQTNFMPMDXn (SEQ ID NO:56), wherein X is any amino acid and n is from about 0 to 15.

In another embodiment, the targeting MRD peptide contains a core sequence selected from:
XnEFAPWTXn where n is from about 0 to 50 amino acid residues (SEQ ID NO: 22);
XnELAPWTXn where n is from about 0 to 50 amino acid residues (SEQ ID NO: 25);
XnEFSPWTXn where n is from about 0 to 50 amino acid residues (SEQ ID NO: 28);
XnELEPWTXn where n is from about 0 to 50 amino acid residues (SEQ ID NO: 31); and
Xn AQQEECEX$_1$X$_2$PWTCEHMXn where n is from about 0 to 50 amino acid residues and X, X$_1$ and X$_2$ are any amino acid (SEQ ID NO:57).

Exemplary peptides containing such core peptides include for example:

AQQEECE<u>FA</u>PWTCEHM; (SEQ ID NO: 21)

AQQEECE<u>FA</u>PWTCEHMGSGSATGGSGSTASSGSGSATHQEECE<u>FA</u>PWTCEHMLE; (SEQ ID NO: 23)

AQQEECE<u>LA</u>PWTCEHM; (SEQ ID NO: 24)

AQQEECE<u>LA</u>PWTCEHMGSGSATGGSGSTASSGSGSATHQEECE<u>LA</u>PWTCEHMLE; (SEQ ID NO: 26)

AQQEECE<u>FS</u>PWTCEHM; (SEQ ID NO: 27)

AQQEECE<u>FS</u>PWTCEHMGSGSATGGSGSTASSGSGSATHQEECE<u>FS</u>PWTCEHMLE 2xConFS; (SEQ ID NO: 29)

AQQEECE<u>LE</u>PWTCEHM; (SEQ ID NO: 30)

AQQEECE<u>LE</u>PWTCEHMGSGSATGGSGSTASSGSGSATHQEECE<u>LE</u>PWTCEHMLE; (SEQ ID NO: 32)

AQQEECE<u>FA</u>PWTCEHMGSGSATGGSGSTASSGSGSATHQEECE<u>LA</u>PWTCEHMLE; (SEQ ID NO: 33)

AQQEECE<u>FA</u>PWTCEHMGSGSATGGSGSTASSGSGSATHQEECE<u>FS</u>PWTCEHMLE; (SEQ ID NO: 34)

and

AQQEECEWDPWTCEHMGSGSATGGSGSTASSGSGSATHQEECEWDPWTCEHMLE. (SEQ ID. NO.: 10)

In one embodiment of the present invention, the target of the MRD is ErbB2. In one embodiment of the present invention, the target of the MRD is ErbB3. In one embodiment of the present invention, the target of the MRD is tumor-associated surface antigen epithelial cell adhesion molecule (Ep-CAM).

In one embodiment of the present invention, the target of the MRD is VEGF. In one aspect, the peptide sequence of the VEGF targeting MRD is VEPNCDIHVMWEWECFERL (SEQ ID. NO.:13).

In one embodiment of the present invention, the target of the MRD is an insulin-like growth factor-I receptor. In one aspect, the peptide sequence of the insulin-like growth factor-I receptor targeting MRD is SFYSCLESLVNGPAEKSRGQWDGCRKK (SEQ ID NO:14). Other illustrative IGF-1R targeting MRDs include, for example, a peptide with the formula NFYQCIX$_1$X$_2$LX$_3$X$_4$X$_5$PAEKSRGQWQECRTGG (SEQ ID NO:58), wherein X$_1$ is E or D; X$_2$ is any amino acid; X$_3$ is any amino acid; X$_4$ is any amino acid and X$_5$ is any amino acid.

Illustrative peptides that contain the formula include:

NFYQCIEMLASHPAEKSRGQWQECRTGG; (SEQ ID NO: 35)

NFYQCIEQLALRPAEKSRGQWQECRTGG; (SEQ ID NO: 36)

NFYQCIDLLMAYPAEKSRGQWQECRTGG; (SEQ ID NO: 37)

```
NFYQCIERLVTGPAEKSRGQWQECRTGG;      (SEQ ID NO: 38)

NFYQCIEYLAMKPAEKSRGQWQECRTGG;      (SEQ ID NO: 39)

NFYQCIEALQSRPAEKSRGQWQECRTGG;      (SEQ ID NO: 40)

NFYQCIEALSRSPAEKSRGQWQECRTGG;      (SEQ ID NO: 41)

NFYQCIEHLSGSPAEKSRGQWQECRTG;       (SEQ ID NO: 42)

NFYQCIESLAGGPAEKSRGQWQECRTG;       (SEQ ID NO: 43)

NFYQCIEALVGVPAEKSRGQWQECRTG;       (SEQ ID NO: 44)

NFYQCIEMLSLPPAEKSRGQWQECRTG;       (SEQ ID NO: 45)

NFYQCIEVFWGRPAEKSRGQWQECRTG;       (SEQ ID NO: 46)

NFYQCIEQLSSGPAEKSRGQWQECRTG;       (SEQ ID NO: 47)

NFYQCIELLSARPAEKSRGQWAECRAG;       (SEQ ID NO: 48)
and

NFYQCIEALARTPAEKSRGQWVECRAP.       (SEQ ID NO: 49)
```

In one embodiment of the present invention, the target of the MRD is a tumor antigen.

In one embodiment of the present invention, the target of the MRD is an epidermal growth factor receptor (EGFR). In one embodiment of the present invention, the target of the MRD is an angiogenic factor. In one embodiment of the present invention, the target of the MRD is an angiogenic receptor.

In one embodiment of the present invention, the MRD is a vascular homing peptide. In one aspect, the peptide sequence of the vascular homing peptide is ACDCRGD-CFCG (SEQ ID. NO:15).

In one embodiment of the present invention, the target of the MRD is a nerve growth factor. In one of the present invention, the antibody binds to a cell surface antigen.

In one embodiment of the present invention, the antibody or MRD binds to EGFR, ErbB2, ErbB3, ErbB4, CD20, insulin-like growth factor-I receptor, or prostate specific membrane antigen. In one aspect, the peptide sequence of the EGFR targeting MRD is VDNKFNKELEKAYNEIRN-LPNLNGWQMTAFIASLVDDPSQSANLLAEAKKLN-DAQA PK (SEQ ID NO: 16). In one aspect, the peptide sequence of the EGFR targeting MRD is VDNKFNKEM-WIAWEEIRNLPNLNGWQMTAFIASLVDDPSQSANL-LAEAKKLNDAQ APK (SEQ ID NO: 17). In one aspect of the present invention, the peptide sequence of ErbB2 targeting MRD is VDNKFNKEMRNAYWEIALLPNLN-NQQKRAFIRSLYDDPSQSANLLAEAKKLNDAQA PK (SEQ ID NO: 18).

In one embodiment of the present invention, the antibody binds to an angiogenic factor.

In one embodiment of the present invention, the antibody binds to an angiogenic receptor.

The present invention also relates to an isolated polynucleotide comprising a nucleotide sequence of the antibody. In one aspect of the present invention, a vector comprises the polynucleotide. In yet another aspect, the polynucleotide is operatively linked with a regulatory sequence that controls expression on the polynucleotide. In one aspect, a host cell comprises the polynucleotide or progeny.

The present invention also relates to a method of treating a disease a subject in need thereof is provided, the method comprising administering an antibody comprising an MRD. In one aspect, the disease is cancer. In another aspect, undesired angiogenesis in inhibited. In yet another aspect, angiogenesis is modulated. In yet another aspect, tumor growth is inhibited. In another embodiment, a method of treatment comprising administering an additional therapeutic agent along with an antibody comprising an MRD is described.

The present invention also relates to a method of making a full length antibody comprising a MRD is described. In one aspect, the MRD is derived from a phage display library. IN another aspect, the MRD is derived from natural ligands.

In one embodiment of the present invention, the antibody is chimeric or humanized.

DETAILED DESCRIPTION OF THE INVENTION

Figure 1:
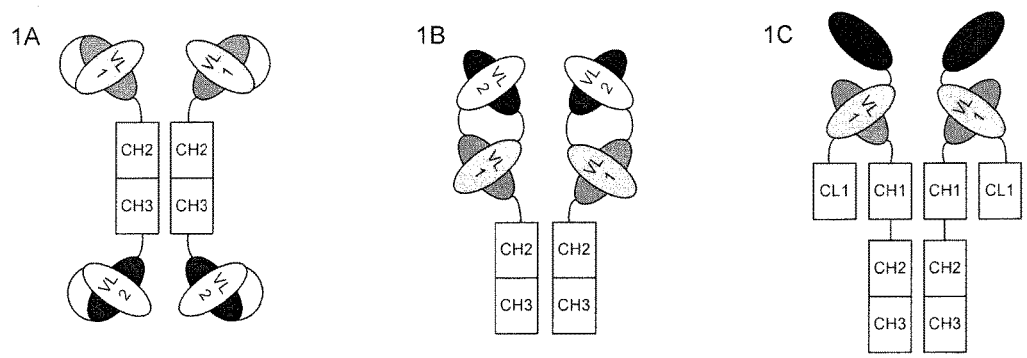
FIG. 1 shows the schematic representation of different designs of tetravalent IgG-like BsAbs.
Figure 2:
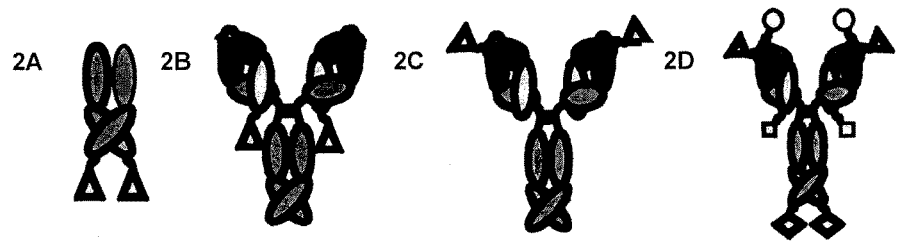
FIG. 2 shows schematic representations of MRD-antibody fusions. (A) a typical peptibody as C-terminal fusion with Fc; (B) an antibody with a C-terminal MRD fusion with the light chain of the antibody; (C) an antibody with an N-terminal MRD fusion with the light chain of the antibody; and (D) an antibody with unique MRD peptides fused to each terminus of the antibody.

The term "antibody" used herein to refer to intact immunoglobulin molecules and includes polyclonal and monoclonal antibodies, chimeric, single chain, and humanized antibodies. An intact antibody comprises at least two heavy (H) chains and two light (L) chains inter-connected by disulfide bonds. Each heavy chain is comprised of a heavy chain variable region (abbreviated herein as VH) and a heavy chain constant region. The heavy chain constant region is comprised of three domains, $CH_1$, $CH_2$ and $CH_3$. Each light chain is comprised of a light chain variable region (abbreviated herein as $V_L$) and a light chain constant region. The light chain constant region is comprised of one domain, $C_L$. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxyl-terminus in the following order: FR1, CDR1, FR2, CDR2, FR3, CDR3, FR4. The variable regions of the heavy and light chains contain a binding domain that interacts with an antigen.

A "dual-specific antibody" is used herein to refer to an immunoglobulin molecule which contain dual-variable-domain immunoglobins, where the dual-variable-domain can be engineered from any two monoclonal antibodies.

An "antibody combining site" is that structural portion of an antibody molecule comprised of a heavy and light chain variable and hypervariable regions that specifically binds (immunoreacts with) an antigen. The term "immunoreact" in its various forms means specific binding between an antigenic determinant-containing molecule and a molecule containing an antibody combining site such as a whole antibody molecule or a portion thereof.

The term "peptibody" refers to a peptide or polypeptide which comprises less than a complete, intact antibody.

The term "naturally occurring" when used in connection with biological materials such as a nucleic acid molecules, polypeptides, host cells, and the like refers to those which are found in nature and not modified by a human being.

"Monoclonal antibody" refers to a population of antibody molecules that contain only one species of antibody combining site capable of immunoreacting with a particular epitope. A monoclonal antibody thus typically displays a single binding affinity for any epitope with which it immunoreacts. A monoclonal antibody may therefore contain an antibody molecule having a plurality of antibody combining sites, each immunospecific for a different epitope, e.g., a bispecific monoclonal antibody.

A "modular recognition domain" (MRD) or "target binding peptide" is a molecule, such as a protein, glycoprotein and the like, that can specifically (non-randomly) bind to a target molecule. The amino acid sequence of a MRD site can tolerate some degree of variability and still retain a degree of capacity to bind the target molecule. Furthermore, changes in the sequence can result in changes in the binding specificity and in the binding constant between a preselected target molecule and the binding site.

"Cell surface receptor" refers to molecules and complexes of molecules capable of receiving a signal and the transmission of such a signal across the plasma membrane of a cell. An example of a cell surface receptor of the present invention is an activated integrin receptor, for example, an activated αvβ3 integrin receptor on a metastatic cell.

The "target binding site" or "target site" is any known, or yet to be described, amino acid sequence having the ability to selectively bind a preselected agent. Exemplary reference target sites are derived from the RGD-dependent integrin ligands, namely fibronectin, fibrinogen, vitronectin, von Willebrand factor and the like, from cellular receptors such as VEGF, ErbB2, vascular homing peptide or angiogenic cytokines, from protein hormones receptors such as insulin-like growth factor-I receptor, epidermal growth factor receptor and the like, and from tumor antigens.

The term "protein" is defined as a biological polymer comprising units derived from amino acids linked via peptide bonds; a protein can be composed of two or more chains.

A "fusion polypeptide" is a polypeptide comprised of at least two polypeptides and optionally a linking sequence to operatively link the two polypeptides into one continuous polypeptide. The two polypeptides linked in a fusion polypeptide are typically derived from two independent sources, and therefore a fusion polypeptide comprises two linked polypeptides not normally found linked in nature.

The term "linker" refers to a peptide located between the antibody and the MRD. Linkers can have from about 2 to 20 amino acids, usually 4 to 15 amino acids.

"Target cell" refers to any cell in a subject (e.g., a human or animal) that can be targeted by the antibody comprising an MRD of the invention. The target cell can be a cell expressing or overexpressing the target binding site, such as activated integrin receptor.

"Patient," "subject," "animal" or "mammal" are used interchangeably and refer to mammals such as human patients and non-human primates, as well as experimental animals such as rabbits, rats, and mice, and other animals. Animals include all vertebrates, e.g., mammals and non-mammals, such as sheep, dogs, cows, chickens, amphibians, and reptiles.

"Treating" or "treatment" includes the administration of the antibody comprising an MRD of the present invention to prevent or delay the onset of the symptoms, complications, or biochemical indicia of a disease, alleviating the symptoms or arresting or inhibiting further development of the disease, condition, or disorder. Treatment can be prophylactic (to prevent or delay the onset of the disease, or to prevent the manifestation of clinical or subclinical symptoms thereof) or therapeutic suppression or alleviation of symptoms after the manifestation of the disease. Treatment can be with the antibody-MRD composition alone, or it can be used in combination with an additional therapeutic agent.

As used herein, the terms "pharmaceutically acceptable," or "physiologically tolerable" and grammatical variations thereof, as they refer to compositions, carriers, diluents and reagents, are used interchangeably and represent that the materials are capable of administration to or upon a human without the production of undesirable physiological effects such as nausea, dizziness, gastric upset and the like.

"Modulate," means adjustment or regulation of amplitude, frequency, degree, or activity. In another related aspect, such modulation may be positively modulated (e.g., an increase in frequency, degree, or activity) or negatively modulated (e.g., a decrease in frequency, degree, or activity).

"Cancer," "tumor," or "malignancy" are used as synonymous terms and refer to any of a number of diseases that are characterized by uncontrolled, abnormal proliferation of cells, the ability of affected cells to spread locally or through the bloodstream and lymphatic system to other parts of the body (metastasize) as well as any of a number of characteristic structural and/or molecular features. A "cancerous," "tumor," or "malignant cell" is understood as a cell having specific structural properties, lacking differentiation and being capable of invasion and metastasis. Examples of cancers are, breast, lung, brain, bone, liver, kidney, colon, head and neck, ovarian, hematopoietic (e.g., leukemia), and prostate cancer.

"Humanized antibody" or "chimeric antibody" includes antibodies in which CDR sequences derived from the germline of another mammalian species, such as a mouse, have been grafted onto human framework sequences.

The present invention describes an approach based on the adaptation of target binding peptides or modular recognition domains (MRDs) as fusions to catalytic or non-catalytic antibodies that provide for effective targeting of tumor cells or soluble molecules while leaving the prodrug activation capability of the catalytic antibody intact. MRDs can also extend the binding capacity of non-catalytic antibodies providing for an effective approach to extend the binding functionality of antibodies, particularly for therapeutic purposes.

One aspect of the present invention relates to development of a full-length antibody comprising a modular recognition domain (MRD). The interaction between a protein ligand and its target receptor site often takes place at a relatively large interface. However, only a few key residues at the interface contribute to most of the binding. Thus, molecules of peptide length (generally 2 to 60 amino acids) can bind to the receptor protein of a given large protein ligand. It is contemplated that MRDs of the present invention contain a peptide sequence that bind to target sites of interests and are about 2 to 60 amino acids.

The role of integrins such as αvβ3 and αvβ5 as tumor-associated markers has been well documented. A recent study of 25 permanent human cell lines established from advanced ovarian cancer demonstrated that all lines were positive for αvβ5 expression and many were positive for αvβ3 expression. Studies have also shown that αvβ3 and αvβ5 is highly expressed on malignant human cervical tumor tissues. Integrins have also demonstrated therapeutic effects in animal models of Kaposi's sarcoma, melanoma, and breast cancer.

A number of integrin αvβ3 and αvβ5 antagonists are in clinical development. These include cyclic RGD peptides and synthetic small molecule RGD mimetics. Two antibody-based integrin antagonists are currently in clinical trials for the treatment of cancer. The first is Vitaxin, the humanized form of the murine anti-human αvβ3 antibody LM609. A dose-escalating phase I study in cancer patients demonstrated that it was safe for use in humans. Another antibody in clinical trials is CNT095, a fully human mAb that recognizes αv integrins. A Phase I study of CNT095 in patients with a variety of solid tumors has shown that it is well tolerated. Cilengitide, a peptide antagonist of αvβ3 and αvβ5, has also proven safe in phase I trials. Furthermore, there has been numerous drug targeting and imaging studies based on the use of ligands for these receptors. These preclinical and clinical observations demonstrate the importance of targeting αvβ3 and αvβ5 and studies involving the use of antibodies in this strategy have consistently reported that targeting through these integrins is safe.

An example of an integrin-binding MRD is an RGD tripeptide-containing binding site, and is exemplary of the general methods described herein. Ligands having the RGD motif as a minimum recognition domain are well known, a partial list of which includes, with the corresponding integrin target in parenthesis, fibronectin (α3β1, α5β1, αvβ1, αIIbβ3, αvβ3, and α3β1) fibrinogen (αMβ2 and αIIbβ1) von Willebrand factor (αIIbβ3 and αvβ3), and vitronectin (αIIbβ3, αvβ3 and αvβ5).

Examples of RGD containing targeting MRDs useful in the present invention have amino acid residue sequences shown below:

|  | |
|---|---|
| YCRGDCT | (SEQ ID. NO.: 3) |
| PCRGDCL | (SEQ ID. NO.: 4) |
| TCRGDCY | (SEQ ID. NO.: 5) |
| LCRGDCF | (SEQ ID. NO.: 6) |

A MRD that mimics a non-RGD-dependent binding site on an integrin receptor and having the target binding specificity of a high affinity ligand that recognizes the selected integrin is also contemplated in the present invention.

Angiogenesis is essential to many physiological and pathological processes. Ang2 has been shown to act as a proangiogenic molecule. Administration of Ang2-selective inhibitors is sufficient to suppress both tumor angiogenesis and corneal angiogenesis. Therefore, Ang2 inhibition alone or in combination with inhibition of other angiogenic factors such as VEGF may represent an effective antiangiogenic strategy for treating patients with solid tumors.

It is contemplated that MRDs useful in the present invention include those that bind to angiogenic receptors, angiogenic factors, and/or Ang-2. Examples of angiogenic cytokine targeting MRD sequences are listed below:
MGAQTNFMPMDDLEQRLYEQFILQQGLE (SEQ ID. NO.: 7)
MGAQTNFMPMDNDELLLYEQFILQQGLE (SEQ ID. NO.: 8)
MGAQTNFMPMDATETRLYEQFILQQGLE (SEQ ID. NO.: 9)
AQQEECEWDPWTCEH-MGSGSATGGSGSTASSGSGSATHQEECEWDPWTCE-HMLE (SEQ ID. NO.: 10) (2×Con4)
MGAQTNFMPMDNDELLNYEQFILQQGLE (SEQ ID. NO.: 11)
PXDNDXLLNY (SEQ ID. NO.: 12) where X is one of the 20 naturally-occurring amino acids
MGAQTNFMPMDNDELLLYEQFILQQG-LEGGSGSTASSGSGSSLGAQTNFMPMDNDE LLLY (SEQ ID NO: 20)
AQQEECEWDPWTCEH-MGSGSATGGSGSTASSGSGSATHQEECEWDPWTCE-HMLE (SEQ ID. NO.: 10)
AQQEECEFAPWTCEHM ConFA (SEQ ID NO:21)
core nEFAPWTn (SEQ ID NO: 22) where n is from about 0 to 50 amino acid residues AQQEECE<u>FA</u>PWTCEHMGSGSATGGSGSTASSGSGSATHQEECE<u>FA</u>PWTCEHMLE (SEQ ID NO: 23) 2×ConFA
AQQEECE<u>LA</u>PWTCEHM (SEQ ID NO: 24) ConLA
XnELAPWTXn where n is from about 0 to 50 amino acid residues and X is any amino acid (SEQ ID NO: 25)
AQQEECE<u>LA</u>PWTCEHMGSGSATGGSGSTASSGSGSATHQEECE<u>LA</u>PWTCEHMLE (SEQ ID NO: 26) 2×ConLA
AQQEECE<u>FS</u>PWTCEHM ConFS (SEQ ID NO: 27)
XnEFSPWTXn where n is from about 0 to 50 amino acid residues and X is any amino acid (SEQ ID NO: 28)
AQQEECE<u>FS</u>PWTCEHMGSGSATGGSGSTASSGSGSATHQEECE<u>FS</u>PWTCEHMLE 2×ConFS (SEQ ID NO: 29)
AQQEECE<u>LE</u>PWTCEHM ConLE (SEQ ID NO: 30)
XnELEPWTXn where n is from about 0 to 50 amino acid residues (SEQ ID NO: 31) and wherein X is any amino acid
AQQEECE<u>LE</u>PWTCEHMGSGSATGGSGSTASSGSGSATHQEECE<u>LE</u>PWTCEHMLE 2×ConLE (SEQ ID NO: 32)

It should be understood that such peptides can be present in dimmers, trimers or other multimers either homologous or heterologous in nature. For example, one can dimerize identical Con-based sequences such as in 2×ConFA to provide a homologous dimer, or the Con peptides can be mixed such that ConFA is combined with ConLA to create ConFA-LA heterodimer with the sequence:

(SEQ ID NO: 33)
AQQEECE<u>FA</u>PWTCEHMGSGSATGGSGSTASSGSGSATHQEECE<u>LA</u>PWTCEHMLE.

Another heterodimer is ConFA combined with ConFS to create ConFA-FS with the sequence:

(SEQ ID NO: 34)
AQQEECE<u>FA</u>PWTCEHMGSGSATGGSGSTASSGSGSATHQEECE<u>FS</u>PWTCEHMLE.

One of skill in the art, given the teachings herein, will appreciate that other such combinations will create functional Ang2 binding MRDs as described herein.

In one aspect, the invention includes a peptide having the sequence:
NFYQCIX$_1$X$_2$LX$_3$X$_4$X$_5$PAEKSRGQWQECRTGG (SEQ ID NO:58), wherein X$_1$ is E or D; X$_2$ is any amino acid; X$_3$ is any amino acid; X$_4$ is any amino acid and X$_5$ is any amino acid.

The invention also includes peptides having a core sequence selected from:
XnEFAPWTXn where n is from about 0 to 50 amino acid residues (SEQ ID NO: 22);
XnELAPWTXn where n is from about 0 to 50 amino acid residues (SEQ ID NO: 25);
XnEFSPWTXn where n is from about 0 to 50 amino acid residues (SEQ ID NO: 28);
XnELEPWTXn where n is from about 0 to 50 amino acid residues (SEQ ID NO: 31); or
Xn AQQEECEX$_1$X$_2$PWTCEHMXn where n is from about 0 to 50 amino acid residues and X, X$_1$ and X$_2$ are any amino acid (SEQ ID NO:57).

Phage display selections and structural studies of VEGF neutralizing peptides in complex with VEGF have been reported. These studies have revealed that peptide v114 (VEPNCDIHVMWEWECFERL) (SEQ ID. NO.: 13) is VEGF specific, binds VEGF with 0.2 µM affinity, and neutralizes VEGF-induced proliferation of Human Umbilical Vein Endothelial Cells (HUVEC). Since VEGF is a homodimer, the peptide occupies two identical sites at either end of the VEGF homodimer. An antibody containing an MRD that targets VEGF is contemplated in the present invention. Anti-VEGF antibodies can be found for example in Cancer Research 57, 4593-4599, October 1997; J Biol Chem 281:10 6625, 2006, herein incorporated by reference.

Insulin-like growth factor-I receptor-specific MRDs can be used in the present invention. One example of an MRD sequence that targets the insulin-like growth factor-I receptor is SFYSCLESLVNGPAEKSRGQWDGCRKK (SEQ ID NO.: 14).

Additional IGF-1R MRDs include the following:

```
                                    (SEQ ID NO: 35)
NFYQCIEMLASHPAEKSRGQWQECRTGG (SEQ ID NO: 36)
NFYQCIEQLALRPAEKSRGQWQECRTGG (SEQ ID NO: 37)
NFYQCIDLLMAYPAEKSRGQWQECRTGG (SEQ ID NO: 38)
NFYQCIERLVTGPAEKSRGQWQECRTGG (SEQ ID NO: 39)
NFYQCIEYLAMKPAEKSRGQWQECRTGG (SEQ ID NO: 40)
NFYQCIEALQSRPAEKSRGQWQECRTGG (SEQ ID NO: 41)
NFYQCIEALSRSPAEKSRGQWQECRTGG (SEQ ID NO: 42)
NFYQCIEHLSGSPAEKSRGQWQECRTG (SEQ ID NO: 43)
NFYQCIESLAGGPAEKSRGQWQECRTG (SEQ ID NO: 44)
NFYQCIEALVGVPAEKSRGQWQECRTG (SEQ ID NO: 45)
NFYQCIEMLSLPPAEKSRGQWQECRTG (SEQ ID NO: 46)
NFYQCIEVFWGRPAEKSRGQWQECRTG (SEQ ID NO: 47)
NFYQCIEQLSSGPAEKSRGQWQECRTG (SEQ ID NO: 48)
NFYQCIELLSARPAEKSRGQWAECRAG (SEQ ID NO: 49)
NFYQCIEALARTPAEKSRGQWVECRAP
```

A number of studies have characterized the efficacy of linking the vascular homing peptide to other proteins like IL-I2 or drugs to direct their delivery in live animals. As such, vascular homing MRDs are contemplated for use in the present invention. One example of an MRD sequence that is a vascular homing peptide is ACDCRGDCFCG (SEQ ID NO.: 15).

Numerous other target binding sites are contemplated by the present invention, including epidermal growth factor receptor (EGFR), CD20, tumor antigens, ErbB2, ErbB3, ErbB4, insulin-like growth factor-I receptor, nerve growth factor (NGR), hepatocyte growth factor receptor, and tumor-associated surface antigen epithelial cell adhesion molecule (Ep-CAM). MRDs can be directed towards these target binding sites.

Examples of MRD sequences that bind to EGFR are listed below:

(SEQ ID. NO.: 16)
VDNKFNKELEKAYNEIRNLPNLNGWQMTAFIASLVDDPSQSANLLAE
AKKLNDAQAPK.

(SEQ ID. NO.: 17)
VDNKFNKEMWIAWEEIRNLPNLNGWQMTAFIASLVDDPSQSANLLAE
AKKLNDAQAPK.

An example of an MRD sequence that bind to ErbB2 is listed below:

(SEQ ID. NO.: 18)
VDNKENKEMRNAYWEIALLPNLNNQQKRAFIRSLYDDPSQSANLLAE
AKKLNDAQAPK.

The sequence of the MRD can be determined several ways. MRD sequences can be derived from natural ligands or known sequences that bind to a specific target binding site can be used. Additionally, phage display technology has emerged as a powerful method in identifying peptides which bind to target receptors. In peptide phage display libraries, random peptide sequences can be displayed by fusion with coat proteins of filamentous phage. The methods for elucidating binding sites on polypeptides using phage display vectors has been previously described, in particular in WO 94/18221. The methods generally involve the use of a filamentous phage (phagemid) surface expression vector system for cloning and expressing polypeptides that bind to the pre-selected target site of interest.

The methods of the present invention for preparing MRDs involve the use of phage display vectors for their particular advantage of providing a means to screen a very large population of expressed display proteins and thereby locate one or more specific clones that code for a desired target binding reactivity. Once the sequence of the MRD has been elucidated, the peptides may be prepared by any of the methods disclosed in the art.

Variants and derivatives of the MRDs are included within the scope of the present invention. Included within variants are insertional, deletional, and substitutional variants as well as variants that include MRDs presented here with additional amino acids at the N- and/or C-terminus, including from about 0 to 50, 0 to 40, 0 to 30, 0 to 20 amino acids and the like. It is understood that a particular MRD of the present invention may contain one, two, or all three types of variants. Insertional and substitutional variants may contain natural amino acids, unconventional amino acids, or both.

It is contemplated that catalytic and non-catalytic antibodies can be used in the present invention. Antibody 38C2 is an antibody-secreting hybridoma, and has been previously described in WO 97/21803. 38C2 contains an antibody combining site that catalyzes the aldol addition reaction between an aliphatic donor and an aldehyde acceptor. In a syngeneic mouse model of neuroblastoma, systemic administration of an etoposide prodrug and intra-tumor injection of Ab 38C2 inhibited tumor growth.

Other antibodies of interest to this invention include A33 binding antibodies. Human A33 antigen is a transmembrane glycoprotein of the Ig superfamily. The function of the human A33 antigen in normal and malignant colon tissue is not yet known, however, several properties of the A33 antigen suggest that it is a promising target for immunotherapy of colon cancer. These properties include (i) the highly restricted expression pattern of the A33 antigen, (ii) the expression of large amounts of the A33 antigen on colon cancer cells, (iii) the absence of secreted or shed A33 antigen, and (iv) the fact that upon binding of antibody A33 to the A33 antigen, antibody A33 is internalized and sequestered in vesicles, and (v) the targeting of antibody A33 to A33 antigen expressing colon cancer in preliminary clinical studies. Fusion of a MRD directed toward A33 to a catalytic or non-catalytic antibody would increase the therapeutic efficacy of A33 targeting antibodies.

The present invention also contemplates the preparation of mono-, bi-, tri-, tetra-, and penta-specific antibodies. It is contemplated that the antibodies used in the present invention may be prepared by any method known in the art.

In the antibody-MRD fusion molecules prepared according to the present invention, the MRD may be attached to an antibody through the peptide's N-terminus or C-terminus. The MRD may be attached to the antibody at the C-terminal end of the heavy chain of the antibody, the N-terminal end of the heavy chain of the antibody, the C-terminal end of the light chain of the antibody, or the N-terminal end of the light chain of the antibody. The MRD may be attached to the antibody directly, or attached through an optional linker peptide, which can be between 2 to 20 peptides long. The linker peptide can contain a short linker peptide with the sequence GGGS (SEQ ID. NO.:1), a medium linker peptide with the sequence SSGGGSGGGGGSS (SEQ ID. NO.: 2), or a long linker peptide with the sequence SSGGGGSGGGGGSSRSS (SEQ ID NO.: 19). The present invention also provides for two or more MRDs which are linked to any terminal end of the antibody. It is also contemplated that two or more MRDs can be directly attached or attached through a linker peptide to two or more terminal ends of the antibody. The multiple MRDs can target the same target binding site, or two or more different target binding sites. Additional peptide sequences may be added to enhance the in vivo stability of the MRD.

The antibody-MRD fusion molecules can be encoded by a polynucleotide comprising a nucleotide sequence. A vector can contain the polynucleotide sequence. The polynucleotide sequence can also be linked with a regulatory sequence that controls expression of the polynucleotide in a host cell. A host cell, or its progeny, can contain the polynucleotide encoding the antibody-MRD fusion molecule.

The present invention contemplates therapeutic compositions useful for practicing the therapeutic methods described herein. Therapeutic compositions of the present invention contain a physiologically tolerable carrier together with at least one species of antibody comprising an MRD as described herein, dissolved or dispersed therein as an active ingredient. In a preferred embodiment, the therapeutic composition is not immunogenic when administered to a human patient for therapeutic purposes.

The preparation of a pharmacological composition that contains active ingredients dissolved or dispersed therein is well understood in the art. Typically such compositions are prepared as sterile injectables either as liquid solutions or suspensions, aqueous or non-aqueous, however, solid forms suitable for solution, or suspensions, in liquid prior to use can also be prepared. The preparation can also be emulsified. Thus, an antibody-MRD containing composition can take the form of solutions, suspensions, tablets, capsules, sustained release formulations or powders, or other compositional forms.

The active ingredient can be mixed with excipients which are pharmaceutically acceptable and compatible with the active ingredient and in amounts suitable for use in the therapeutic methods described herein. Suitable excipients are, for example, water, saline, dextrose, glycerol, ethanol or the like and combinations thereof. In addition, if desired, the composition can contain minor amounts of auxiliary substances such as wetting or emulsifying agents, pH buffering agents and the like which enhance the effectiveness of the active ingredient.

The therapeutic composition of the present invention can include pharmaceutically acceptable salts of the components therein. Pharmaceutically acceptable salts include the acid addition salts (formed with the free amino groups of the polypeptide) that are formed with inorganic acids such as, for example, hydrochloric or phosphoric acids, or such organic acids as acetic, tartaric, mandelic and the like. Salts formed with the free carboxyl groups can also be derived from inorganic bases such as, for example, sodium, potassium, ammonium, calcium or ferric hydroxides, and such organic bases as isopropylamine, trimethylamine, 2-ethylamino ethanol, histidine, procaine and the like.

Physiologically tolerable carriers are well known in the art. Exemplary of liquid carriers are sterile aqueous solutions that contain no materials in addition to the active ingredients and water, or contain a buffer such as sodium phosphate at physiological pH value, physiological saline or both, such as phosphate-buffered saline. Still further, aqueous carriers can contain more than one buffer salt, as well as salts such as sodium and potassium chlorides, dextrose, propylene glycol, polyethylene glycol, and other solutes.

Liquid compositions can also contain liquid phases in addition to and to the exclusion of water.

Exemplary of such additional liquid phases are glycerin, vegetable oils such as cottonseed oil, organic esters such as ethyl oleate, and water-oil emulsions.

A therapeutic composition contains an antibody comprising a MRD of the present invention, typically in an amount of at least 0.1 weight percent of antibody per weight of total therapeutic composition. A weight percent is a ratio by weight of antibody to total composition. Thus, for example, 0.1 weight percent is 0.1 grams of antibody-MRD per 100 grams of total composition.

An antibody-containing therapeutic composition typically contains about 10 microgram (ug) per milliliter (ml) to about 100 milligrams (mg) per ml of antibody as active ingredient per volume of composition, and more preferably contains about 1 mg/ml to about 10 mg/ml (i.e., about 0.1 to 1 weight percent).

A therapeutic composition in another embodiment contains a polypeptide of the present invention, typically in an amount of at least 0.1 weight percent of polypeptide per weight of total therapeutic composition. A weight percent is a ratio by weight of polypeptide to total composition. Thus, for example, 0.1 weight percent is 0.1 grams of polypeptide per 100 grams of total composition.

Preferably, an polypeptide-containing therapeutic composition typically contains about 10 microgram (ug) per milliliter (ml) to about 100 milligrams (mg) per ml of polypeptide as active ingredient per volume of composition, and more preferably contains about 1 mg/ml to about 10 mg/ml (i.e., about 0.1 to 1 weight percent).

In view of the benefit of using humanized or chimeric antibodies in vivo in human patients, the presently described antibody-MRD molecules are particularly well suited for in vivo use as a therapeutic reagent. The method comprises administering to the patient a therapeutically effective amount of a physiologically tolerable composition containing an antibody comprising a MRD of the invention.

The dosage ranges for the administration of the antibody comprising a MRD of the invention are those large enough to produce the desired effect in which the disease symptoms mediated by the target molecule are ameliorated. The dosage should not be so large as to cause adverse side effects, such as hyperviscosity syndromes, pulmonary edema, congestive heart failure, and the like. Generally, the dosage will vary with the age, condition, sex and extent of the disease in the patient and can be determined by one of skill in the art. The dosage can be adjusted by the individual physician in the event of any complication.

A therapeutically effective amount of an antibody comprising a MRD of this invention is typically an amount of antibody such that when administered in a physiologically tolerable composition is sufficient to achieve a plasma concentration of from about 0.1 microgram (ug) per milliliter (ml) to about 100 ug/ml, preferably from about 1 ug/ml to about 5 ug/ml, and usually about 5 ug/ml. Stated differently, the dosage can vary from about 0.1 mg/kg to about 300 mg/kg, preferably from about 0.2 mg/kg to about 200 mg/kg, most preferably from about 0.5 mg/kg to about 20 mg/kg, in one or more dose administrations daily, for one or several days.

The antibody comprising a MRD of the invention can be administered parenterally by injection or by gradual infusion over time. Although the target molecule can typically be accessed in the body by systemic administration and therefore most often treated by intravenous administration of therapeutic compositions, other tissues and delivery means are contemplated where there is a likelihood that the tissue targeted contains the target molecule. Thus, antibodies comprising a MRD of the invention can be administered intravenously, intraperitoneally, intramuscularly, subcutaneously, intracavity, transdermally, and can be delivered by peristaltic means.

The therapeutic compositions containing a human monoclonal antibody or a polypeptide of this invention are conventionally administered intravenously, as by injection of a unit dose, for example. The term "unit dose" when used in reference to a therapeutic composition of the present invention refers to physically discrete units suitable as unitary dosage for the subject, each unit containing a predetermined quantity of active material calculated to produce the desired therapeutic effect in association with the required diluent; i.e., carrier, or vehicle.

The compositions are administered in a manner compatible with the dosage formulation, and in a therapeutically effective amount. The quantity to be administered depends on the subject to be treated, capacity of the subject's system to utilize the active ingredient, and degree of therapeutic effect desired. Precise amounts of active ingredient required to be administered depend on the judgment of the practitioner and are peculiar to each individual. However, suitable dosage ranges for systemic application are disclosed herein and depend on the route of administration. Suitable regimes for administration are also variable, but are typified by an initial administration followed by repeated doses at one or more hour intervals by a subsequent injection or other administration. Alternatively, continuous intravenous infusion sufficient to maintain concentrations in the blood in the ranges specified for in vivo therapies are contemplated.

The following examples are intended to illustrate but not limit the invention.

EXAMPLES

Example 1. Integrin Targeting Antibody-MRD Molecules

Novel antibody-MRD fusion molecules were prepared by fusion of an integrin $\alpha v \beta 3$-targeting peptides to catalytic antibody 38C2. Fusions at the N-termini and C-termini of the light chain and the C-termini of the heavy chain were most effective. Using flow cytometry, the antibody conjugates were shown to bind efficiently to integrin αvβ3-expressing human breast cancer cells. The antibody conjugates also retained the retro-aldol activity of their parental catalytic antibody 38C2, as measured by methodol and doxorubicin prodrug activation. This demonstrates that cell targeting and catalytic antibody capability can be efficiently combined for selective chemotherapy.

Example 2. Angiogenic Cytokine Targeting Antibody-MRD Molecules

Angiogenic cytokine targeting antibody-MRD fusion molecules were constructed. The antibody used was 38C2, which was fused with a MRD containing the 2×Con4 peptide (AQQEECEWDPWTCEHMGSGSATGGSGSTASSGSGSATHQEECEWDPWTCEHMLE (SEQ ID. NO.: 10)). The MRD peptide was fused to either the N- or C-terminus of the light chain and the C-terminus of the heavy chain. Similar results were found with the other Ang-2 MRD peptides. Additional Ang-2 MRD peptides include:
LM-2×-32
MGAQTNFMPMDNDELLLYEQFILQQG-LEGGSGSTASSGSGSSLGAQTNFMPMDNDE LLLY (SEQ ID NO:20)
AQQEECEWDPWTCEH-MGSGSATGGSGSTASSGSGSATHQEECEWDPWTCE-HMLE (2×Con4) (SEQ ID. NO.: 10)
AQQEECEFAPWTCEHM ConFA (SEQ ID NO:21)
core XnEFAPWTXn where n is from about 0 to 50 amino acid residues (SEQ ID NO:22)
AQQEECE FAPWTCEHMGSGSATGGSGSTASSGSGSATHQEECE FAPWTCEHMLE 2×ConFA (SEQ ID NO:23)
AQQEECELAPWTCEHM ConLA (SEQ ID NO:24)
XnELAPWTXn where n is from about 0 to 50 amino acid residues (SEQ ID NO:25)
AQQEECE LAPWTCEHMGSGSATGGSGSTASSGSGSATHQEECE LAPWTCEHMLE 2×ConLA (SEQ ID NO:26)
AQQEECEFSPWTCEHM ConFS (SEQ ID NO:27)
XnEFSPWTXn where n is from about 0 to 50 amino acid residues (SEQ ID NO:28)
AQQEECE FSPWTCEHMGSGSATGGSGSTASSGSGSATHQEECE FSPWTCEHMLE 2×ConFS (SEQ ID NO:29)
AQQEECELEPWTCEHM ConLE (SEQ ID NO:30)
XnELEPWTXn where n is from about 0 to 50 amino acid residues (SEQ ID NO:31)
AQQEECE LEPWTCEHMGSGSATGGSGSTASSGSGSATHQEECE LEPWTCEHMLE 2×ConLE (SEQ ID NO:32).

It should be understood that such peptides can be present in dimmers, trimers or other multimers either homologous or heterologous in nature. For example, one can dimerize identical Con-based sequences such as in 2×ConFA to provide a homologous dimer, or the Con peptides can be mixed such that ConFA is combined with ConLA to create ConFA-LA heterodimer with the sequence:

(SEQ ID NO: 33)
AQQEECEFAPWTCEHMGSGSATGGSGSTASSGSGSATHQEECELAPW TCEHMLE.

Another illustrative heterodimer is ConFA combined with ConFS to create ConFA-FS with the sequence:

(SEQ ID NO: 34)
AQQEECEFAPWTCEHMGSGSATGGSGSTASSGSGSATHQEECEFSPW TCEHMLE.

One of skill in the art, given the teachings herein, will appreciate that other such combinations will create functional Ang2 binding MRDs as described herein.

Example 3. Antibody-MRD Fusions with Non-Catalytic Antibodies

A humanized mouse monoclonal antibody, LM609, directed towards human integrin αvβ3 has been previously described. (Rader, C. et. al., 1998. Rader C, Cheresh D A, Barbas C F 3rd. Proc Natl Acad Sci USA. 1998 Jul. 21; 95(15):8910-5).

Figure 3:
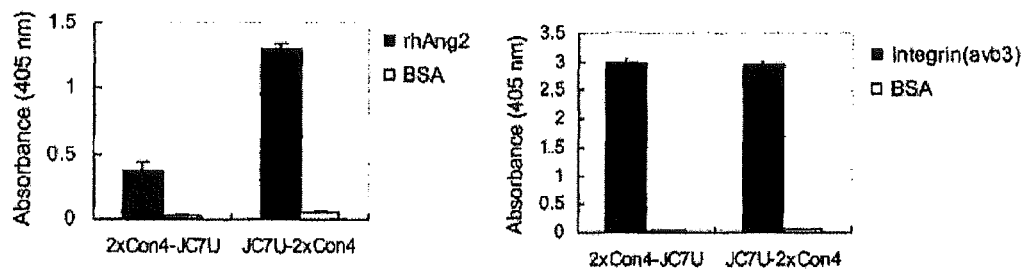
FIG. 3 depicts the results of an ELISA in which integrin and Ang2 were bound by an anti-integrin antibody fused to an ang-2 targeting MRD.
Figure 4:
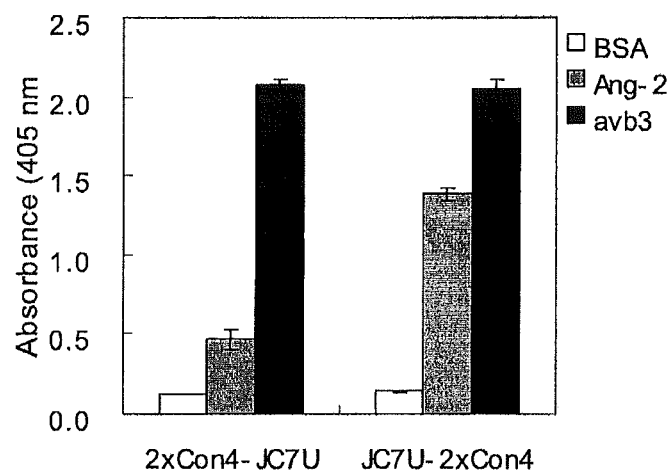
FIG. 4 depicts the results of an ELISA in which integrin and Ang2 were bound by an anti-integrin antibody fused to an ang-2 targeting MRD.

A human non-catalytic monoclonal Ab, JC7U was fused to an anti-Ang2 MRD containing 2×Con4 (AQQEECEWDPWTCEHMGSGSATGGSGSTASSGSGSATHQEECEWDPWTCEHMLE (SEQ ID. NO.: 10)) at either the N- or C-terminus of the light chain. 2×Con4 (AQQEECEWDPWTCEHMGSGSATGGSGSTASSGSGSATHQEECEWDPWTCEHMLE (SEQ ID. NO.: 10)) was studied as an N-terminal fusion to the Kappa chain of the antibody (2×Con4-JC7U) and as a C-terminal fusion (JC7U-2×Con4). Both fusions maintained integrin and Ang2 binding. As shown in the left panel of FIG. 3, both antibody constructs (2×Con4-JC7U and JC7U-2×Con4) specifically bound to recombinant Ang2 as demonstrated by ELISA studies. Binding to Ang2, however, is significantly higher with JC7U-2×Con4, which has the 2×Con4 (SEQ ID. NO.: 10) fusion at the C-terminus of the light chain of the antibody. The right panel of FIG. 3 depicts the binding of Ang2-JC7U and JC7U-Ang2 to integrin αvβ3. The results show that fusion of 2×Con4 (SEQ ID. NO.: 10) to either the N- or the C-light chain terminus does not affect mAb JC7U binding to integrin αvβ3. FIG. 4 depicts another ELISA study using the same antibody-MRD fusion constructs.

Example 4. Herceptin-MRD Fusion Molecules

Another example of MRD fusions to a non-catalytic antibody are Herceptin-MRD fusion constructs. The Herceptin-MRD fusions are multifunctional, both small-molecule αv integrin antagonists and the chemically programmed integrin-targeting antibody show remarkable efficacy in preventing the breast cancer metastasis by interfering with αv-mediated cell adhesion and proliferation. MRD fusions containing Herceptin-2×Con4 (which targets ErbB2 and ang2) and Herceptin-V114 (which targets ErbB2 and VEGF targeting) and Herceptin-RGD-4C-2×Con4 (which targets ErbB2, ang2, and integrin targeting) are effective.

Example 5. VEGF Targeting Antibody-MRD Molecules

An antibody containing an MRD that targets VEGF was constructed. A MRD which targets v114 (SEQ ID. NO. 13) was fused at the N-terminus of the kappa chain of 38C2 and Herceptin using the long linker sequence (SEQ ID. NO. 2). Expression and testing of the resulting antibody-MRD fusion constructs demonstrated strong VEGF binding.

Example 6. IGF-1R Targeting Antibody-MRD Molecules

Fusion of an MRD which targets the IGF-1R (SFYSCLESLVNGPAEKSRGQWDGCRKK (SEQ ID. NO.: 14)) to the N-terminus of the kappa chain of 38C2 and Herceptin using the long linker sequence as a connector was studied. Expression and testing of the resulting antibody-MRD fusion constructs demonstrated strong IGF-1R binding. Additional clones showing high binding to IGR-1R were also identified after several rounds of mutagenesis and screening. The preferred sequences listed below show no significant or no binding affinity to the insulin receptor. (see Table 2).

TABLE 1

Template for further mutagenesis:

| | | | | |
|---|---|---|---|---|
| Rm2-2-218 | GTGGAGTGCAGGGCGCCG | VECRAP | SEQ ID NO: | 50, 51 |
| Rm2-2-316 | GCTGAGTGCAGGGCTGGG | AECRAG | SEQ ID NO: | 52, 53 |
| Rm2-2-319 | CAGGAGTGCAGGACGGGG | QECRTG | SEQ ID NO: | 54, 55 |

TABLE 2

| Mutant | Amino acid sequence | Template | SEQ ID NO: |
|---|---|---|---|
| Rm4-31 | NFYQCIEMLASHPAEKSRGQWQECRTGG | Rm2-2-319 | 35 |
| Rm4-33 | NFYQCIEQLALRPAEKSRGQWQECRTGG | Rm2-2-319 | 36 |
| Rm4-39 | NFYQCIDLLMAYPAEKSRGQWQECRTGG | Rm2-2-319 | 37 |
| Rm4-310 | NFYQCIERLVTGPAEKSRGQWQECRTGG | Rm2-2-319 | 38 |
| Rm4-314 | NFYQCIEYLAMKPAEKSRGQWQECRTGG | Rm2-2-319 | 39 |
| Rm4-316 | NFYQCIEALQSRPAEKSRGQWQECRTGG | Rm2-2-319 | 40 |
| Rm4-319 | NFYQCIEALSRSPAEKSRGQWQECRTGG | Rm2-2-319 | 41 |
| Rm4-44 | NFYQCIEHLSGSPAEKSRGQWQECRTG | Rm2-2-319 | 42 |
| Rm4-45 | NFYQCIESLAGGPAEKSRGQWQECRTG | Rm2-2-319 | 43 |
| Rm4-46 | NFYQCIEALVGVPAEKSRGQWQECRIG | Rm2-2-319 | 44 |
| Rm4-49 | NFYQCIEMLSLPPAEKSRGQWQECRTG | Rm2-2-319 | 45 |
| Rm4-410 | NEYQCIEVFWGRPAEKSRGQWQECRTG | Rm2-2-319 | 46 |
| Rm4-411 | NFYQCIEQLSSGPAEKSRGQWQECRTG | Rm2-2-319 | 47 |
| Rm4-415 | NFYQCIELLSARPAEKSRGQWAECRAG | Rm2-2-316 | 48 |
| Rm4-417 | NFYQCIEALARTPAEKSRGQWVECRAP | Rm2-2-218 | 49 |

Example 7. ErbB2 Binding, Ang-2-Targeting Antibody-MRD Molecules

Figure 5:
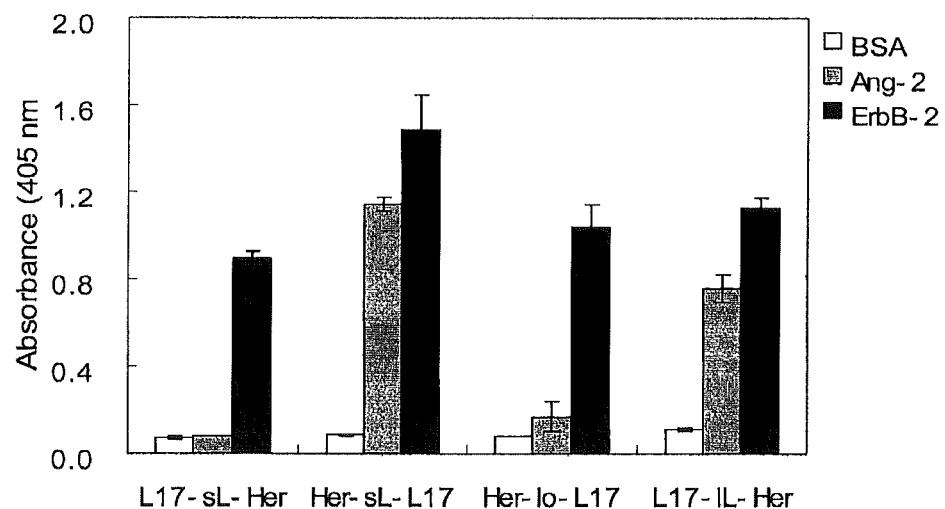
FIG. 5 depicts the results of an ELISA in which an anti-ErbB2 antibody was fused to an MRD which targeted Ang2.

An antibody was constructed which contains an MRD that targets Ang-2 (L17) fused to the light chain of an antibody which binds to ErbB2. Either the short linker sequence, the long linker sequence, or the 4th loop in the light chain constant region was used as a linker. FIG. 5 depicts the results of an ELISA using constructs containing an N-terminal fusion of Ang-2 targeting MRD with the ErbB2 antibody with the short linker peptide (GGGS (SEQ ID NO.: 1)) (L17-sL-Her), a C-terminal fusion of Ang-2 targeting MRD with the ErbB2 antibody with the short linker peptide (Her-sL-L17), a C-terminal fusion of Ang-2 targeting MRD with the ErbB2 antibody with the 4th loop in the light chain constant region (Her-lo-L17), or an N-terminal fusion of Ang-2 targeting MRD with the ErbB2 antibody with the long linker peptide (SSGGGGSGGGGGGSSRSS (SEQ ID NO.: 19)) (L17-lL-Her). ErbB2 was bound with varying degrees by all of the constructs. However, Ang-2 was bound only by Her-sL-L17 and L17-lL-Her.

Figure 6:
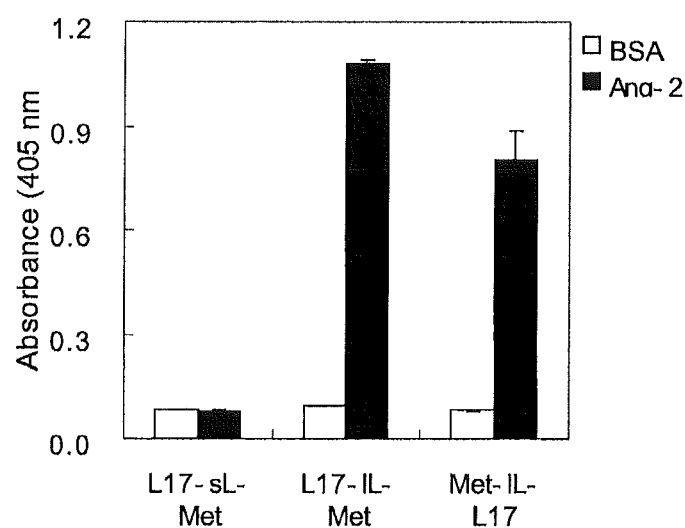
FIG. 6 depicts the results of an ELISA in which an Ang2 targeting MRD was fused to a hepatocyte growth factor receptor binding antibody.

Example 8. Hepatocyte Growth Factor Receptor Binding, Ang-2-Targeting Antibody-MRD Molecules Fusion of an MRD which targets Ang-2 (L17) was made to either the N-terminus or C-terminus of the light chain of the Met antibody, which binds to hepatocyte growth factor receptor. Either the short linker sequence or the long linker sequence were used as a connector. FIG. 6 depicts the results of an ELISA using constructs containing N-terminal fusion of Ang-2 targeting MRD with the Met antibody with the short linker peptide (GGGS (SEQ ID NO.: 1)) (L17-sL-Met), N-terminal fusion of Ang-2 targeting MRD with the Met antibody with the long linker peptide (SSGGGGSGGGGGGSSRSS (SEQ ID NO.: 19)) (L17-lL-Met), and C-terminal fusion of Ang-2 targeting MRD with the Met antibody with the long linker peptide (Met-iL-L17). Expression and testing of the resulting antibody-MRD fusion constructs demonstrated strong Ang-2 binding when the long linker peptide was used. Fusion of the Ang-2 targeting MRD to the C-light chain terminus of the antibody resulted in slightly higher binding to Ang-2 then fusion of the Ang-2 targeting to the N-light chain terminus of the antibody.

Example 9. ErbB2 Binding, Integrin-Targeting Antibody-MRD Molecules

Figure 7:
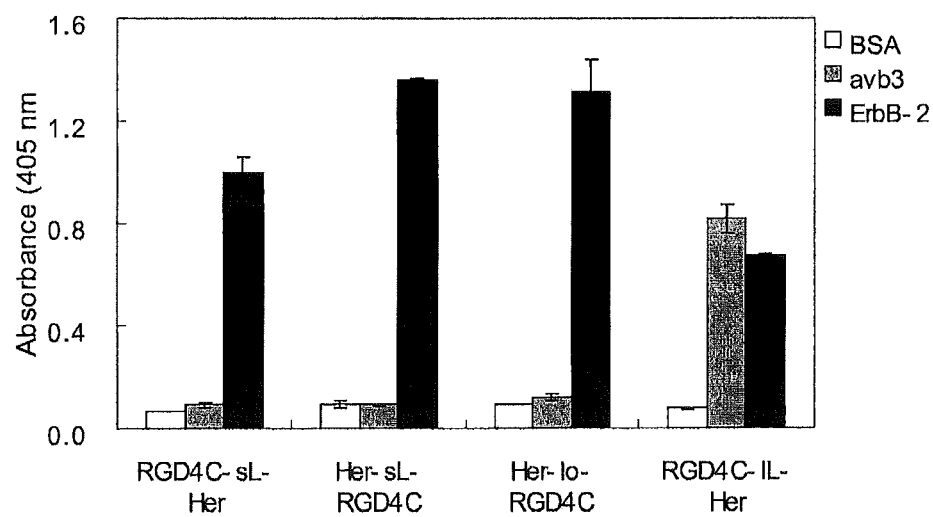
FIG. 7 depicts the results of an ELISA in which an integrin targeting MRD was fused to an ErbB2 binding antibody.

An antibody was constructed which contains an MRD that targets integrin αvβ3 (RGD4C) fused to the light chain of an antibody Herceptin which binds to ErbB2 (Her). Either the short linker sequence, the long linker sequence, or the 4th loop in the light chain constant region was used as a linker. FIG. 7 depicts the results of an ELISA using constructs containing an N-terminal fusion of integrin αvβ3 targeting MRD with the ErbB2 antibody with the short linker peptide (GGGS (SEQ ID NO.: 1)) (RGD4C-sL-Her), a C-terminal fusion of integrin αvβ3 targeting MRD with the ErbB2 antibody with the short linker peptide (Her-sL-RGD4C), a C-terminal fusion of integrin αvβ3 targeting MRD with the ErbB2 antibody with the 4th loop in the light chain constant region (Her-lo-RGD4C), or an N-terminal fusion of integrin αvβ3 targeting MRD with the ErbB2 antibody with the long linker peptide (SSGGGGSGGGGGGSSRSS (SEQ ID NO.: 19)) (RGD4C-lL-Her). ErbB2 was bound with varying degrees by all of the constructs. However, integrin αvβ3 was bound only by RGD4C-lL-Her.

Figure 8:
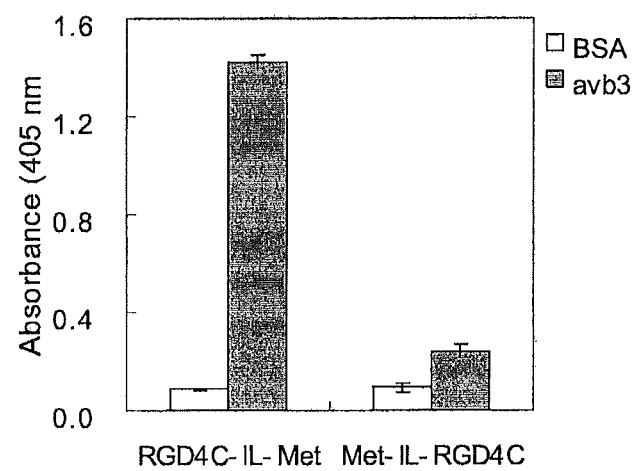
FIG. 8 depicts the results of an ELISA in which an integrin targeting MRD was fused to an hepatocyte growth factor receptor binding antibody.

Example 10. Hepatocyte Growth Factor Receptor Binding, Integrin-Targeting Antibody-MRD Molecules An antibody was constructed which contains an MRD that targets integrin αvβ3 (RGD4C) fused to the light chain of an antibody which binds to the hepatocyte growth factor receptor (Met). Antibody-MRD constructs containing the long linker sequence were used. FIG. 8 depicts the results of an ELISA using constructs containing an N-terminal fusion of integrin αvβ3 targeting MRD with the hepatocyte growth factor receptor antibody (RGD4C-lL-Met), or a C-terminal fusion of integrin αvβ3 targeting MRD with the hepatocyte growth factor receptor antibody (Met-lL-RGD4C). The RGD4C-lL-Met demonstrated strong integrin αvβ3 binding.

Figure 9:
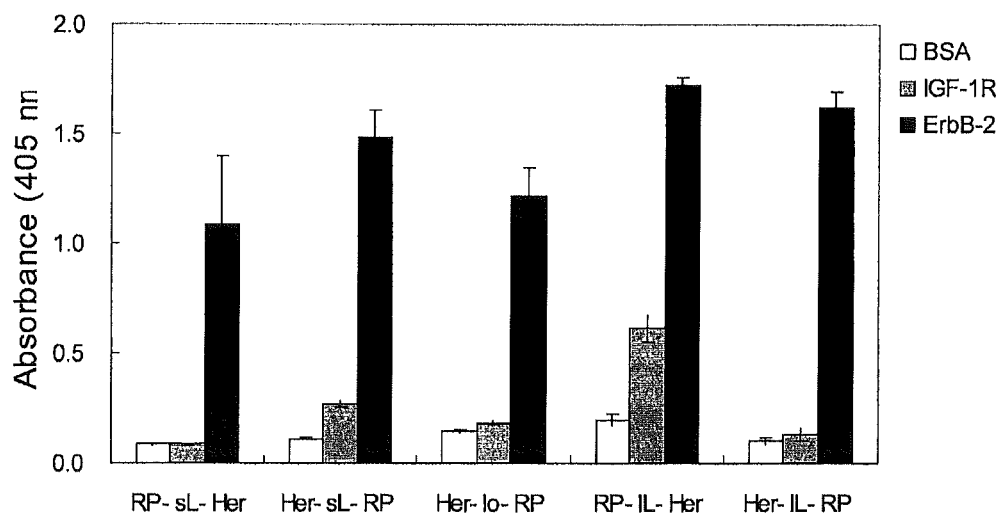
FIG. 9 depicts the results of an ELISA in which an insulin-like growth factor-I receptor targeting MRD was fused to an ErbB2 binding antibody.

Example 11. ErbB2 Binding, Insulin-Like Growth Factor-I Receptor-Targeting Antibody-MRD Molecules Antibodies were constructed which contains an MRD that targets insulin-like growth factor-I receptor (RP) fused to the light chain of an antibody which binds to ErbB2 (Her). Either the short linker peptide, the long linker peptide, or the 4th loop in the light chain constant region was used as a linker. (Carter et al., Proc Natl Acad Sci USA. 1992 May 15; 89(10):4285-9. PMID: 1350088 [PubMed—indexed for MEDLINE]; U.S. Pat. No. 5,677,171; ATCC Deposit 10463, all incorporated by reference herein). FIG. 9 depicts the results of an ELISA using constructs containing an N-terminal fusion of insulin-like growth factor-I receptor targeting MRD with the ErbB2 antibody with the short (RP-sL-Her), a C-terminal fusion of insulin-like growth factor-I receptor targeting MRD with the ErbB2 antibody and the short linker peptide (Her-sL-RP), a C-terminal fusion of insulin-like growth factor-I receptor targeting MRD with the ErbB2 antibody with the 4th loop in the light chain constant region (Her-lo-RP), an N-terminal fusion of insulin-like growth factor-I receptor targeting MRD with the ErbB2 antibody with the long linker peptide (RP-lL-Her), or a C-terminal fusion of insulin-like growth factor-I receptor targeting MRD with the ErbB2 antibody with the long linker peptide (Her-lL-RP). ErbB2 was bound with varying degrees by all of the constructs. Insulin-like growth factor-I receptor was bound by RP-lL-Her.

Example 12. ErbB2 Binding, VEGF-Targeting Antibody-MRD Molecules

Figure 10:
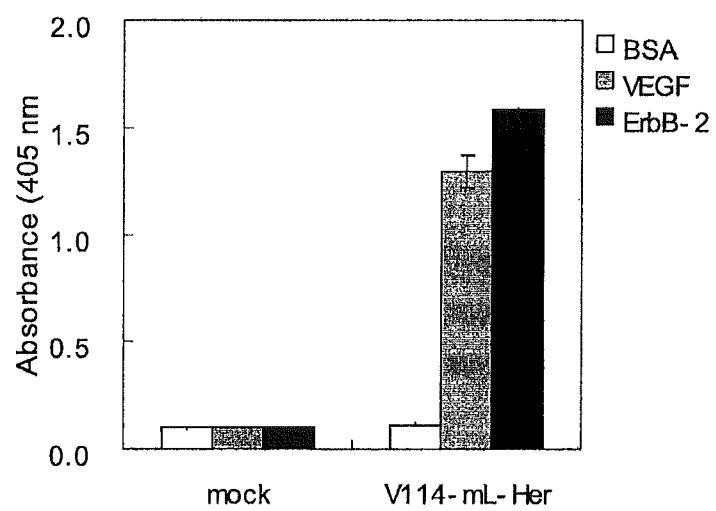
FIG. 10 depicts the results of an ELISA in which a VEGF-targeting MRD was fused to an ErbB2 binding antibody.

Fusion of an MRD which targets VEGF (V114) was made to the N-terminus of the the light chain of a ErbB2-binding antibody (Her). A medium linker peptide (SSGGGGSGGGGGSS (SEQ ID NO.: 2)) was used as a connector. FIG. 10 depicts the results of an ELISA using a construct containing an N-terminal fusion of VEGF targeting MRD with the ErbB2-binding antibody with the medium linker peptide (V114-mL-Her). Expression and testing of the resulting antibody-MRD fusion construct demonstrated strong VEGF and ErbB2 binding.

Example 13. Integrin Targeting Antibody-MRD Molecules

Figure 11:
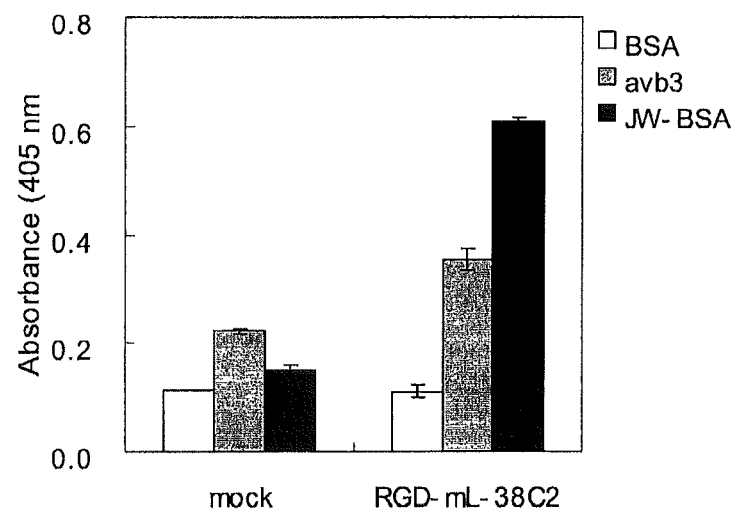
FIG. 11 depicts the results of an ELISA in which an integrin targeting MRD was fused to a catalytic antibody.

Fusion of an MRD which targets integrin αvβ3 (RGD) to the N-terminus of the light chain of 38C2 using the medium linker peptide as a connector was studied. FIG. 11 demonstrates that expression and testing of the resulting antibody-MRD fusion construct had strong integrin αvβ3 binding.

Example 14. Ang-2 Targeting Antibody-MRD Molecules

Figure 12:
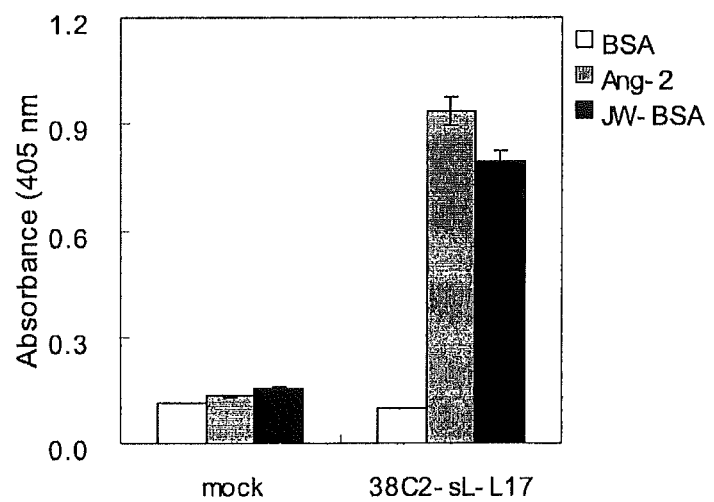
FIG. 12 depicts the results of an ELISA in which an Ang-2-targeting MRD was fused to a catalytic antibody.

Fusion of an MRD which targets Ang-2 (L17) to the C-terminus of the light chain of 38C2 using the short linker sequence as a connector was studied. FIG. 12 demonstrates that expression and testing of the resulting antibody-MRD fusion construct had strong Ang-2 binding.

Example 15. ErbB2 Binding, Integrin and Ang-2 Targeting Antibody-MRD Molecules

Figure 13:
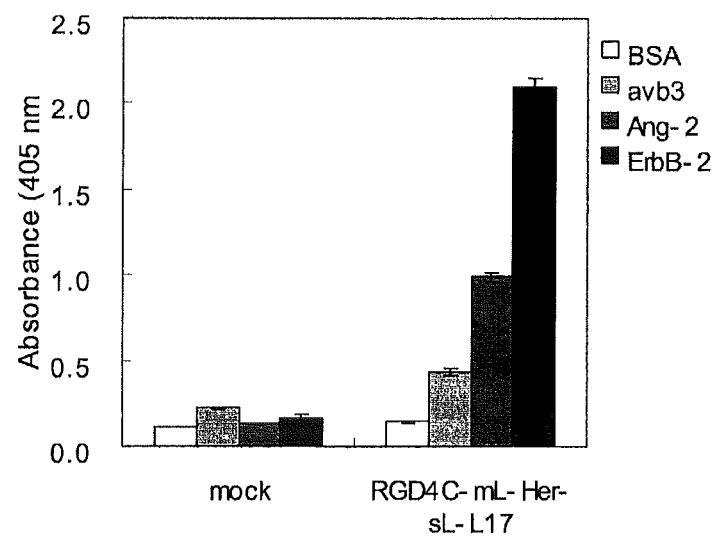
FIG. 13 depicts the results of an ELISA in which an integrin and Ang-2 targeting MRD was fused to an ErbB2 binding antibody.

An MRD which targets integrin αvβ3 (RGD4C) was connected to the N-terminus of the light chain of an ErbB2 targeting antibody (Her) with a medium linker, and an Ang-2 (L17) targeting MRD was connected by a short linker to the C-terminus of the same ErbB2 targeting antibody (RGD4C-mL-Her-sL-L17). FIG. 13 demonstrates that the resulting antibody-MRD fusion construct bound to integrin, Ang-2, and ErbB2.

Example 16. ErbB2 Binding, Integrin-Targeting Antibody-MRD Molecules

Figure 14:
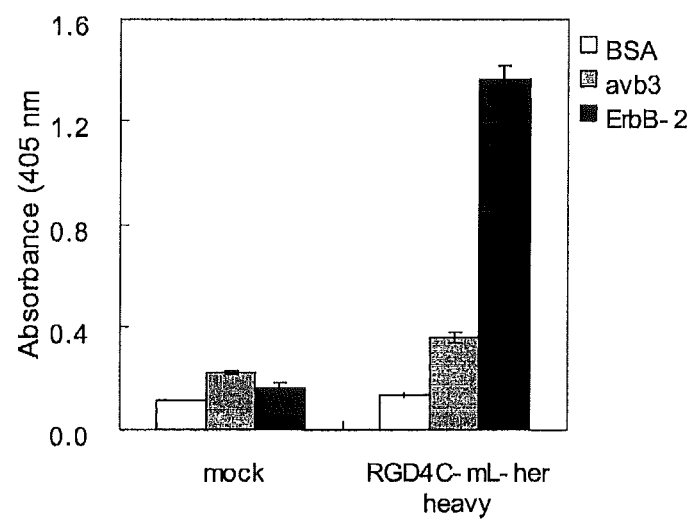
FIG. 14 depicts the results of an ELISA in which an integrin targeting MRD was fused to an ErbB2-binding antibody.

An antibody was constructed which contains an MRD that targets integrin αvβ3 (RGD4C) fused to the N-terminus of the heavy chain of an antibody which binds to ErbB2 (Her) using the medium linker as a connector (RGD4C-mL-her-heavy). FIG. 14 depicts the results of an ELISA using the construct. Both integrin and ErbB2 were bound by the construct.

Figure 15:
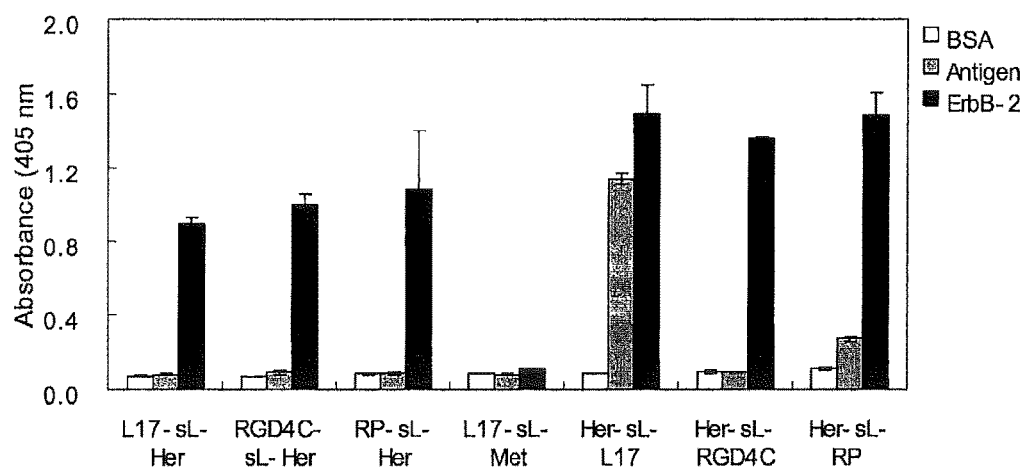
FIG. 15 depicts the results of an ELISA in which an integrin, Ang-2, or insulin-like growth factor-I receptor-targeting MRD was fused to an ErbB2 or hepatocyte growth factor receptor-binding antibody with a short linker peptide.

Example 17. ErbB2 or Hepatocyte Growth Factor Receptor Binding, and Integrin, Ang-2 or Insulin-Like Growth Factor-I Receptor-Targeting Antibody-MRD Molecules with the Short Linker Peptide Antibody-MRD molecules were constructed which contain ErbB2 or hepatocyte growth factor receptor binding antibodies, and integrin αvβ3, Ang-2 or insulin-like growth factor-I receptor-targeting MRD regions were linked with the short linker peptide to the light chain of the antibody. FIG. 15 depicts the results of an ELISA using constructs containing an N-terminal fusion of Ang-2 targeting MRD fused to the ErbB2 antibody (L17-sL-Her), an N-terminal fusion of integrin-targeting MRD with the ErbB2 antibody (RGD4C-sL-Her), an N-terminal fusion of insulin-like growth factor-I receptor targeting MRD with the ErbB2 binding antibody (RP-sL-Her), a C-terminal fusion of Ang-2 targeting MRD with the hepatocyte growth factor receptor binding antibody (L17-sL-Met), a C-terminal fusion of Ang-2 targeting MRD with the ErbB2 binding antibody (Her-sL-L17), a C-terminal fusion of integrin targeting MRD with the ErbB2 binding antibody (Her-sL-RGD4C), or a C-terminal fusion of insulin-like growth factor-I receptor targeting MRD with the ErbB2 binding antibody (Her-sL-RP). ErbB2 was bound with varying degrees by the antibody-MRD constructs, with the exception of the construct containing the hepatocyte growth factor receptor-binding antibody. Antigen was bound only by the Her-sL-L17 construct.

Figure 16:
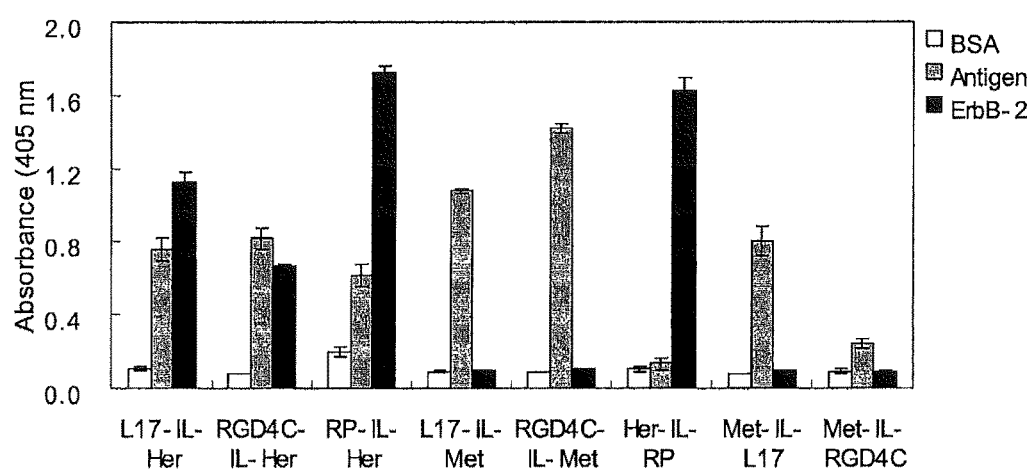
FIG. 16 depicts the results of an ELISA in which an integrin, Ang-2, or insulin-like growth factor-I receptor-targeting MRD was fused to an ErbB2 or hepatocyte growth factor receptor-binding antibody with a long linker peptide.

Example 18. ErbB2 or Hepatocyte Growth Factor Receptor Binding, and Integrin, Ang-2 or Insulin-Like Growth Factor-I Receptor-Targeting Antibody-MRD Molecules with the Long Linker Peptide Antibody-MRD molecules were constructed which contain ErbB2 or hepatocyte growth factor receptor binding antibodies, and integrin αvβ3, Ang-2 or insulin-like growth factor-I receptor-targeting MRD regions linked with the long linker peptide to the light chain of the antibody. FIG. 16 depicts the results of an ELISA using constructs containing an N-terminal fusion of Ang-2 targeting MRD fused to the ErbB2 antibody (L17-lL-Her), an N-terminal fusion of integrin-targeting MRD with the ErbB2 antibody (RGD4C-lL-Her), an N-terminal fusion of insulin-like growth factor-I receptor-targeting MRD with the ErbB2 binding antibody (RP-lL-Her), a C-terminal fusion of Ang-2 targeting MRD with the hepatocyte growth factor receptor binding antibody (L17-lL-Met), a C-terminal fusion of integrin targeting MRD with the hepatocyte growth factor receptor binding antibody (RGD4C-lL-Met), a C-terminal fusion of Ang-2 targeting MRD with the insulin-like growth factor-I receptor binding antibody (Her-lL-RP), a C-terminal fusion of Ang-2 targeting MRD with the the hepatocyte growth factor receptor binding antibody (Met-lL-L17), or a C-terminal fusion of integrin targeting MRD with the the hepatocyte growth factor receptor binding antibody (Met-lL-RGD4C). As shown in FIG. 16, antibody-MRD fusions are effective to bind antigen and ErbB2. Lu et al. J Biol Chem. 2005 May 20; 280(20):19665-72. Epub 2005 Mar. 9; Lu et al. J Biol Chem. 2004 Jan. 23; 279(4):2856-65. Epub 2003 Oct. 23, Although the invention has been described with reference to the above examples, it will be understood that modifications and variations are encompassed within the spirit and scope of the invention. Accordingly, the invention is limited only by the following claims.

What is claimed is:

1. An antibody fusion protein comprising a full length antibody and a modular recognition domain (MRD), wherein the MRD binds to integrin and consists of the amino acid sequence set forth in any one of SEQ ID NOs: 3-6, wherein the MRD is operably linked to the antibody, and wherein the antibody binds to ErbB2.

2. The antibody fusion protein of claim 1, wherein the antibody and the MRD are operably linked through a linker peptide.

3. The antibody fusion protein of claim 2, wherein the linker peptide comprises a sequence selected from the group consisting of: GGGS (SEQ ID NO: 1), SSGGGGSGGGGGGSS (SEQ ID NO: 2), and SSGGGGSGGGGGGSSRSS (SEQ ID NO: 19).

4. The antibody fusion protein of claim 1, wherein the MRD is operably linked to the C-terminal end of the heavy chain of the antibody, the N-terminal end of the heavy chain of the antibody, the C-terminal end of the light chain of the antibody, or the N-terminal end of the light chain of the antibody.

5. The antibody fusion protein of claim 1, wherein the antibody is a chimeric or humanized antibody.

6. The antibody fusion protein of claim 1, wherein the antibody is Trastuzumab.

7. The antibody fusion protein of claim 2, wherein the antibody is a chimeric or humanized antibody.

8. The antibody fusion protein of claim 2, wherein the antibody is Trastuzumab.

9. A method of treating a disease characterized by undesired angiogenesis, comprising administering to a subject in need thereof the antibody fusion protein of claim 1.

* * * * *